(12) United States Patent
Nishino et al.

(10) Patent No.: US 8,173,969 B2
(45) Date of Patent: May 8, 2012

(54) RADIATION DETECTING APPARATUS AND RADIATION IMAGE CAPTURING SYSTEM

(75) Inventors: Naoyuki Nishino, Minami-ashigara (JP); Yasuhiro Seto, Minami-ashigara (JP); Yutaka Yoshida, Fuchu (JP); Keiji Tsubota, Minami-ashigara (JP); Yasunori Ohta, Yokohama (JP); Eiichi Kito, Minami-ashigara (JP); Shinji Imai, Hadano (JP)

(73) Assignee: FUJIFILM Corporation, Tokyo (JP)

( * ) Notice: Subject to any disclaimer, the term of this patent is extended or adjusted under 35 U.S.C. 154(b) by 355 days.

(21) Appl. No.: 12/585,735

(22) Filed: Sep. 23, 2009

(65) Prior Publication Data

US 2010/0072379 A1    Mar. 25, 2010

(30) Foreign Application Priority Data

Sep. 25, 2008  (JP) ................................. 2008-245997

(51) Int. Cl.
*G01T 1/24*        (2006.01)
(52) U.S. Cl. ................................. 250/370.08
(58) Field of Classification Search ............. 250/370.01, 250/370.08, 370.09, 370.11, 370.14; 378/98.8
See application file for complete search history.

(56) References Cited

U.S. PATENT DOCUMENTS

| | | | |
|---|---|---|---|
| 6,856,670 | B2 | 2/2005 | Hoheisel |
| 2003/0031296 | A1* | 2/2003 | Hoheisel ...................... 378/98.8 |
| 2005/0139783 | A1* | 6/2005 | Kubota et al. ............. 250/484.4 |
| 2006/0239412 | A1* | 10/2006 | Jakob et al. ................... 378/189 |
| 2008/0054182 | A1* | 3/2008 | Yokoyama et al. ....... 250/370.09 |
| 2009/0010391 | A1* | 1/2009 | Kito et al. ........................ 378/97 |
| 2009/0026377 | A1* | 1/2009 | Kuwabara et al. ....... 250/370.08 |

FOREIGN PATENT DOCUMENTS

| | | |
|---|---|---|
| JP | 2000-105297 | 4/2000 |
| JP | 2003-70776 | 3/2003 |
| JP | 2006-337184 | 12/2006 |

* cited by examiner

*Primary Examiner* — Mark R Gaworecki
(74) *Attorney, Agent, or Firm* — Jean C. Edwards, Esq.; Edwards Neils PLLC

(57) ABSTRACT

A radiation detecting apparatus includes a flexible radiation conversion panel for detecting radiation that has passed through a subject and converting the detected radiation into radiation image information, and grips disposed on ends of the radiation conversion panel. A hardness of the grips is greater than that of the radiation conversion panel. Holes are formed in the grips for enabling the grips to be gripped.

12 Claims, 31 Drawing Sheets

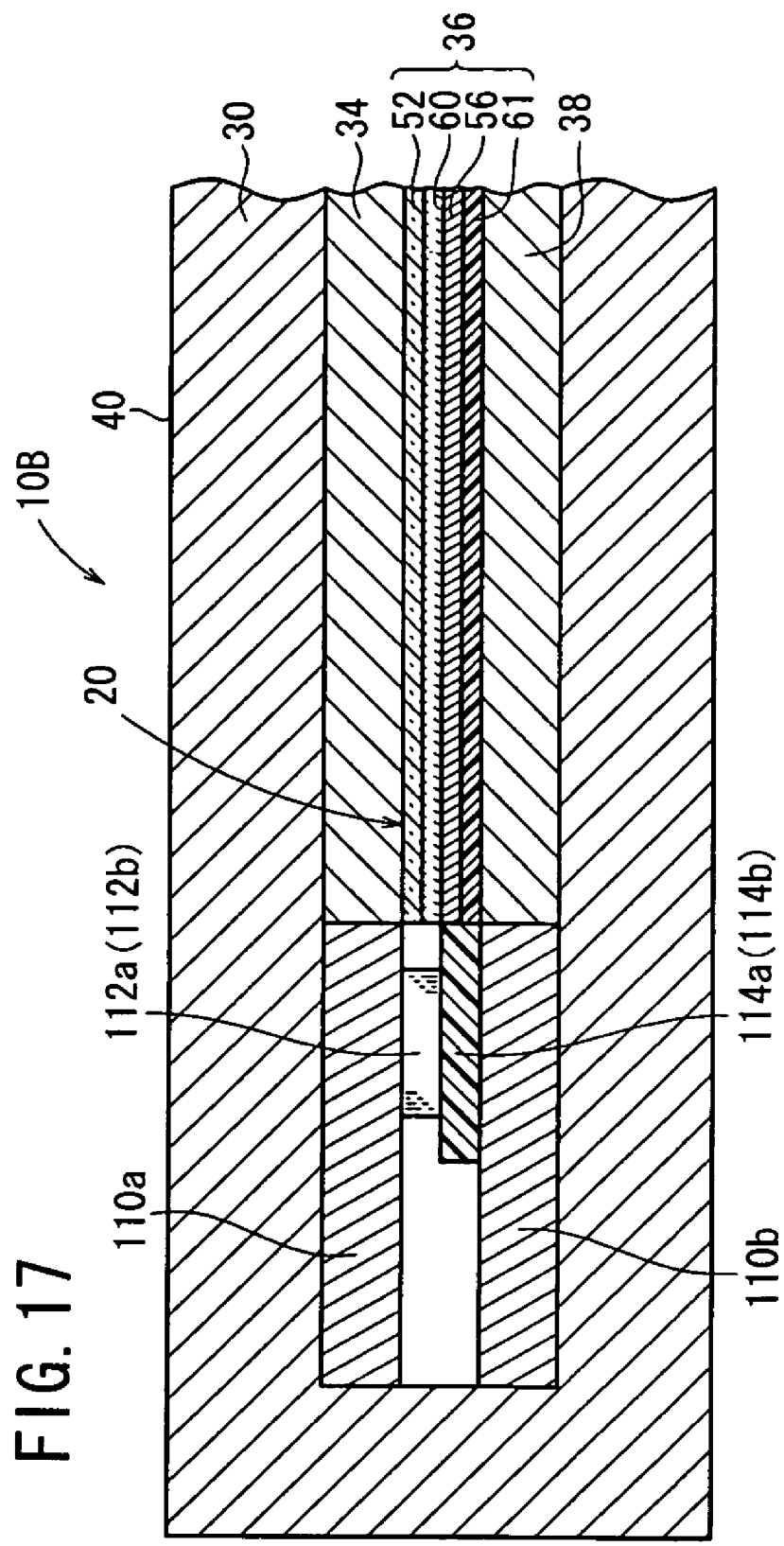

RADIATION DETECTING APPARATUS AND RADIATION IMAGE CAPTURING SYSTEM

CROSS-REFERENCE TO RELATED APPLICATION

This application is based upon and claims the benefit of priority from Patent Application No. 2008-245997 filed on Sep. 25, 2008, in the Japan Patent Office, of which the contents are incorporated herein by reference.

BACKGROUND OF THE INVENTION

1. Field of the Invention

The present invention relates to a radiation detecting apparatus having a radiation conversion panel for detecting radiation that has passed through a subject and converting the detected radiation into radiation image information. The present invention further concerns a radiation image capturing system incorporating such a radiation detecting apparatus therein.

2. Description of the Related Art

In the medical field, there have widely been used radiation image capturing systems, which apply radiation to a subject and guide the radiation that has passed through the subject to a radiation conversion panel, which in turn captures a radiation image from such radiation. Known forms of radiation conversion panels include a conventional radiation film for recording a radiation image by way of exposure, and a stimulable phosphor panel for storing radiation energy representing a radiation image in a phosphor, and reproducing the radiation image as stimulated light by applying stimulating light to the phosphor.

The radiation film, with the radiation image recorded therein, is supplied to a developing device to develop the radiation image. Alternatively, the stimulable phosphor panel is supplied to a reading device in order to read the radiation image as a visible image.

In an operating room or the like, it is necessary to read recorded radiation image information immediately from a radiation conversion panel after the radiation image information has been captured therein for the purpose of quickly and appropriately treating the patient. As a radiation conversion panel which meets such a requirement, there has been developed a direct-conversion-type radiation detector including solid-state detectors for directly converting radiation into electric signals, or an indirect-conversion-type radiation detector comprising a scintillator for temporarily converting radiation into visible light, and solid-state detectors for converting the visible light into electric signals to read detected radiation image information.

Heretofore, there has been proposed a radiation detecting apparatus housing therein a radiation detector (radiation conversion panel), which is flexible enough to match itself to desired surface shapes of the patient, as disclosed in Japanese Laid-Open Patent Publication No. 2003-070776.

However, with the conventional technique according to Japanese Laid-Open Patent Publication No. 2003-070776, because the radiation detector is flexible, when a radiological technician grasps and carries the radiation detector, the radiation detector becomes deformed and handling thereof is difficult. Further, the radiation detector cannot be arranged independently in an upstanding or self-sustaining manner, so that accommodation and storage of the radiation detector is troublesome.

Further, it is commonplace, when used in a hospital or the like, for the radiation detecting apparatus to have a planar shape, and the doctor performs an inspection assuming that a visible image of the patient (subject) based on radiation image information is captured using a planar radiation detecting apparatus. Accordingly, at a time when the subject is exposed to radiation (when capturing a radiation image), it is desirable for a radiation conversion panel (an irradiated surface or image capturing surface) of the radiation detecting apparatus to be positioned flatwise with respect to the subject.

However, in the radiation detecting apparatus of Japanese Laid-Open Patent Publication No. 2003-070776, because the radiation conversion panel is flexible and the radiation conversion panel is arranged in conformity with the surface shape of the subject, it is difficult for the radiation conversion panel to assume a planar shape with respect to the subject when an image is captured.

Further, in Japanese Laid-Open Patent Publication No. 2006-337184, a radiation detector is disclosed in which a scintillator disposed inside a casing is covered with a protective resin layer. In this case, since the protective resin layer is disposed so as to cover an upper surface side of the scintillator, even if an external force is imposed on the scintillator that forms the detecting surface of the radiation detector, the scintillator can be protected against the external force by the protective resin layer.

However, in the conventional technique of Japanese Laid-Open Patent Publication No. 2006-337184, when the radiation detectors are placed in storage, it is presumed that the radiation detectors will be stored in a stacked condition. In this case, when another radiation detector is stacked on an upper side of the protective resin layer, surface damage (lesions, flaws, etc.) to the protective resin layer occurs, and as a result, there is a concern that noise will be generated in the radiation image as a result of scattering caused by such surface damage.

Further, in Japanese Laid-Open Patent Publication No. 2006-337184, examples are proposed in which a sensor panel and a scintillator panel are hermetically sealed by a protective resin layer in a position opposing the casing, or in which the sensor panel and the scintillator panel are hermetically sealed by a protective resin layer formed on upper and lower sides thereof.

However, in the radiation detecting apparatus of Japanese Laid-Open Patent Publication No. 2003-070776, the flexible radiation detector simply is accommodated within a case, which itself is similarly flexible. Accordingly, in Japanese Laid-Open Patent Publication No. 2003-070776, nothing is proposed concerning configurations for protecting the scintillator inside the radiation detector, for example, for protecting the scintillator against moisture or humidity, etc.

Further, in Japanese Laid-Open Patent Publication No. 2006-337184, because the sensor panel and the scintillator panel, which themselves are rigid, are sealed hermetically by the protective resin layer, no consideration is given with respect to any type of flexible radiation detector.

SUMMARY OF THE INVENTION

A first object of the present invention is to improve the handling and workability of a flexible radiation conversion panel at times when the radiation conversion panel is moved and stored.

A second object of the present invention is to provide a flexible radiation conversion panel, which can easily be made to assume a flat planar shape.

A third object of the present invention is to reliably protect the detection surface of a flexible radiation conversion panel, in the case that the radiation conversion panels are stacked and placed in storage.

A fourth object of the present invention is to improve reliability of a radiation detecting apparatus and a radiation image capturing system, by enhancing resistance to moisture and humidity, and enhancing impact resistance of a flexible radiation conversion panel.

To achieve the first object, in accordance with the present invention, a radiation detecting apparatus is provided, comprising a flexible radiation conversion panel for detecting radiation that has passed through a subject and converting the detected radiation into radiation image information, and a grip disposed on an end of the radiation conversion panel, a hardness of the grip being greater than that of the radiation conversion panel, and wherein a hole is provided in the grip for enabling the grip to be gripped.

According to the present invention, a grip having a hardness greater than that of the radiation conversion panel is disposed on an end of a flexible radiation conversion panel, with a hole being provided in the grip. Owing thereto, when the radiation conversion panel is moved, handling of the radiation conversion panel is favorable by gripping the grip, and the radiation conversion panel can be reliably and easily moved to a desired position. Further, for example, by inserting the hole over a hook or the like and hanging it on the hook, the flexible radiation conversion panel can easily and safely be placed in storage.

To achieve the second object, in accordance with the present invention, a radiation detecting apparatus is provided, comprising a flexible radiation conversion panel for detecting radiation that has passed through a subject and converting the detected radiation into radiation image information, and a shape-memory member made of a shape-memory material, which maintains the radiation conversion panel in a planar shape with respect to the subject.

In accordance with the present invention, because the flexible radiation conversion panel is maintained in a planar shape with respect to the subject by means of the shape-memory member, the radiation conversion panel (an image capturing surface of the radiation detecting apparatus) can easily be made to assume a planar shape.

Further, to achieve the third object, in accordance with the present invention, a radiation detecting apparatus is provided comprising a flexible radiation conversion panel for detecting radiation that has passed through a subject and converting the detected radiation into radiation image information, and a protective member disposed on a surface which is opposite to a surface irradiated with the radiation and having a coefficient of friction less than that of the irradiated surface.

According to the present invention, a protective member having a coefficient of friction less than that of an irradiated surface of the flexible radiation conversion panel is disposed on a surface opposite to the surface thereof irradiated with radiation having passed through a subject. As a result, even in the case that a plurality of radiation detecting apparatus are stacked and stored before and after capturing of radiation images, the protective member, which is disposed on a surface opposite to the irradiated surface of the radiation detecting apparatus and has a coefficient of friction less than that of the irradiated surface, abuts against the irradiated surface of another adjacent radiation detecting apparatus. Owing thereto, the irradiated surfaces can be prevented from becoming damaged by the stacked radiation detecting apparatus. As a result, a plurality of radiation detecting apparatus can be stacked and stored in a condition such that the irradiated surfaces thereof are reliably protected.

Still further, to achieve the fourth object, in accordance with the present invention a radiation detecting apparatus is provided comprising a flexible radiation conversion panel for detecting radiation that has passed through a subject and converting the detected radiation into radiation image information, and a sealing protective film that covers at least a portion or the entirety of the radiation conversion panel and which is made of a material permeable to the radiation.

Further, for achieving the fourth object, according to the present invention, a radiation image capturing system is provided comprising the aforementioned radiation detecting apparatus, a radiation source for emitting radiation, and a controller for controlling the radiation source and the radiation detecting apparatus.

According to the present invention, resistance to moisture and humidity, and impact resistance of a flexible radiation conversion panel can be improved, whereby the reliability of a radiation detecting apparatus and a radiation image capturing system can be enhanced. In addition, the radiation image capturing apparatus can be subjected to antiseptic cleaning as necessary, so that a single radiation image capturing apparatus can be used repeatedly and continuously, which also leads to lowering running costs thereof.

The above and other objects, features, and advantages of the present invention will become more apparent from the following description when taken in conjunction with the accompanying drawings in which preferred embodiments of the present invention are shown by way of illustrative example.

BRIEF DESCRIPTION OF THE DRAWINGS

FIG. 17 is a cross-sectional view taken along line XVII-XVII of FIG. 12;

DESCRIPTION OF THE PREFERRED EMBODIMENTS

Figure 1:
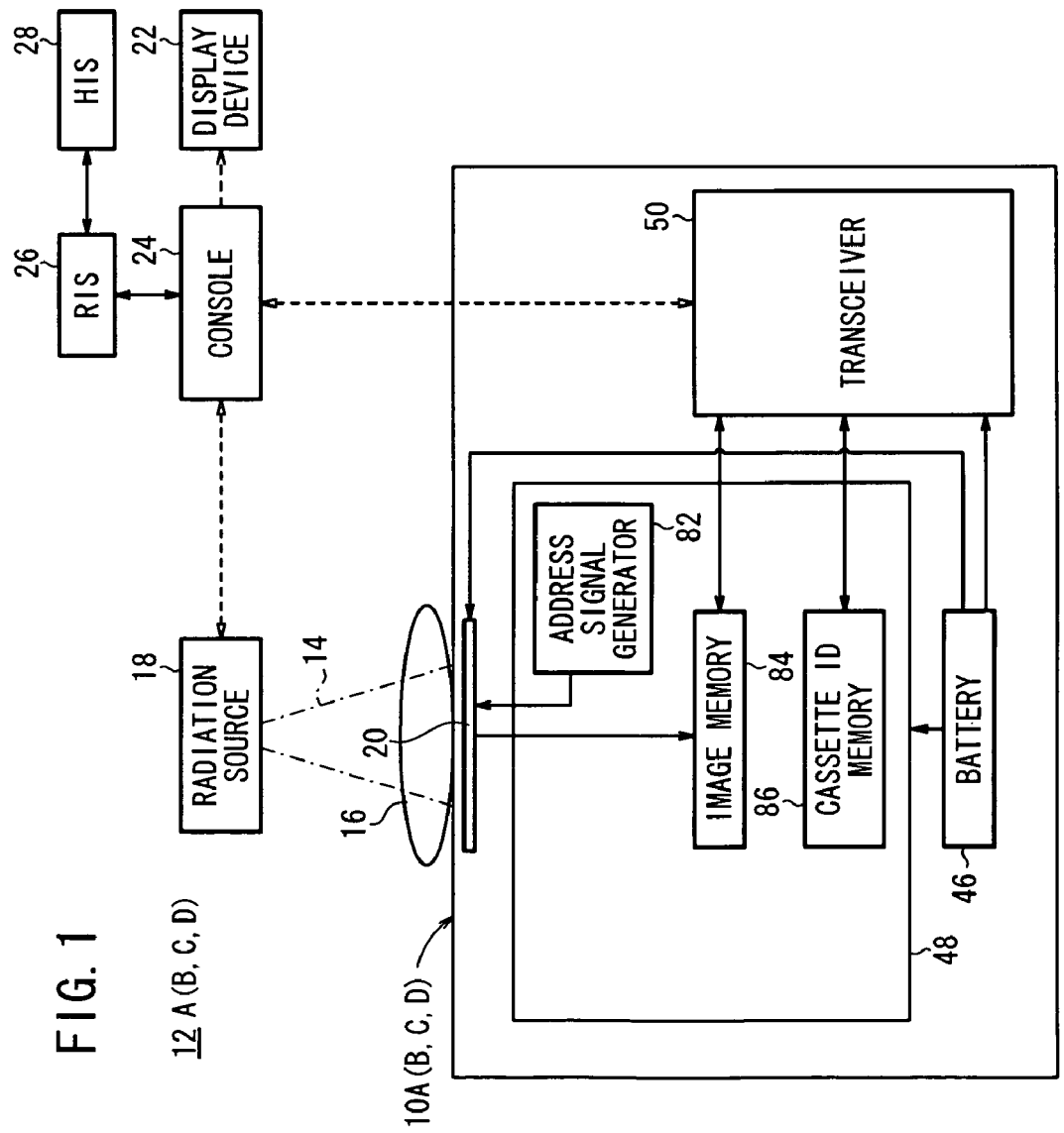
FIG. 1 is a block diagram of a radiation detecting apparatus and a radiation image capturing system according to a first embodiment of the present invention.
Figure 2:
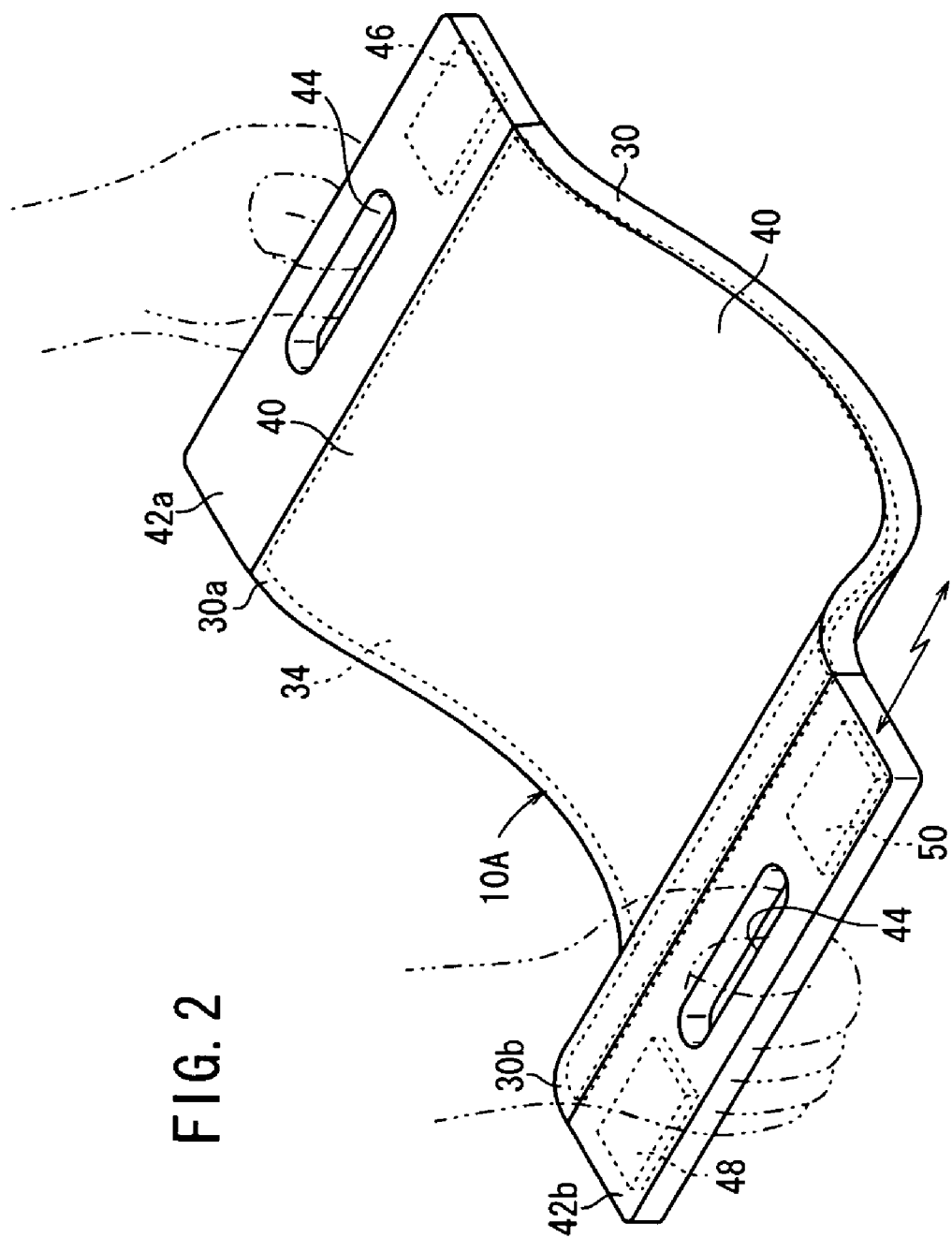
FIG. 2 is a perspective view showing a gripped state of the radiation detecting apparatus of FIG. 1.

Like or corresponding parts are denoted by like or corresponding reference characters throughout the views.

First, a radiation detecting apparatus (hereinafter also referred to as a "radiation detecting cassette") 10A according to a first embodiment of the present invention, and a radiation image capturing system 12A incorporating the radiation detecting cassette 10A therein, will be described below with reference to FIGS. 1 through 11.

As shown in FIG. 1, the radiation image capturing system 12A according to the first embodiment of the present invention includes a radiation source 18 for irradiating a patient 16 as a subject with radiation 14 at a dose depending on image capturing conditions, a radiation detecting cassette 10A having a radiation detector (radiation conversion panel) 20 for detecting radiation 14 that has passed through the patient 16, a display device 22 for displaying radiation image information based on the radiation 14 which has been detected by the radiation detector 20, and a console (controller) 24 for controlling the radiation detecting cassette 10A, the radiation source 18, and the display device 22.

Signals are sent and received between the console 24, the radiation detecting cassette 10A, the radiation source 18, and the display device 22, based on wireless LAN (Local Area Network) communications or wireless millimeter-wave communications such as UWB (Ultra-WideBand) technology, IEEE 802.11.a/g/n, or the like.

The console 24 is connected to a radiology information system (RIS) 26, which generally manages radiation image information handled by the radiological department of the hospital, together with other information. The RIS 26 is connected to a hospital information system (HIS) 28, which generally manages medical information within the hospital.

As shown in FIGS. 2 through 5, the radiation detecting cassette 10A is in the form of a sheet, comprising a screen 30 that serves as a casing made from a material permeable to radiation 14 and which is flexible, wherein the screen 30 is laid out in a substantially flatwise shape against the patient 16 (see FIGS. 3 and 4) at a time when the patient 16 is exposed to radiation 14 (when capturing a radiation image).

The screen 30 is made of a flexible resin such as polyethylene (PE), polyethylene terephthalate (PET), polyvinyl chloride (PVC), polyvinylidene chloride (PVDC), polylactic acid (PLA), polypropylene (PP), polyamide (PA), polycarbonate (PC), polytetrafluoroethylene (PTFE), polyurethane (PU), polystyrene (PS), polyester, an ABS resin, acrylic resin (PMMA), polyacetal (POW, or the like, or from a sheet metal such as aluminum, aluminum oxide, stainless steel, or the like.

The screen 30 houses therein a grid 34 for removing scattered rays of radiation 14 from the patient 16, a sensor substrate 36 of a radiation detector 20 for detecting radiation 14 that has passed through the patient 16, and a lead sheet 38 for absorbing back scattered rays from the radiation 14, which are successively arranged in this order from an irradiated surface (image-capturing surface) 40 facing the patient 16. The grid 34, the radiation detector 20 (sensor substrate 36), and the lead sheet 38 are flexible overall. Further, the irradiated surface 40 of the screen 30 may be constructed as the grid 34.

A pair of grips 42a, 42b, which project a predetermined width from opposite ends 30a, 30b of the screen 30, are disposed respectively on the opposite ends 30a, 30b along the longitudinal direction (the direction of arrow A in FIG. 3) of the screen 30. The grips 42a, 42b are made from rigid bodies formed from a resin material, for example. Substantially elliptical shaped holes 44 are provided respectively in central portions of the grips 42a, 42b. More specifically, in the radiation detecting cassette 10A, the centrally disposed screen 30 thereof is deformable, whereas the grips 42a, 42b, which are disposed on opposite ends 30a, 30b of the screen 30, are rigid and therefore non-deformable. Stated otherwise, the grips 42a, 42b are set with a hardness (rigidity) which is greater than that of the flexible screen 30.

Additionally, by gripping the pair of grips 42a, 42b with both hands, a doctor or a radiological technician can easily carry and move the radiation detecting cassette 10A.

The invention is not limited to the case of providing grips 42a, 42b respectively on both opposite ends 30a, 30b of the screen. One of the grips 42a, 42b may be disposed on either one of the ends 30a or 30b only, or respective grips may be provided so as to surround the circumferential edges of the screen 30 as a whole.

Figure 3:
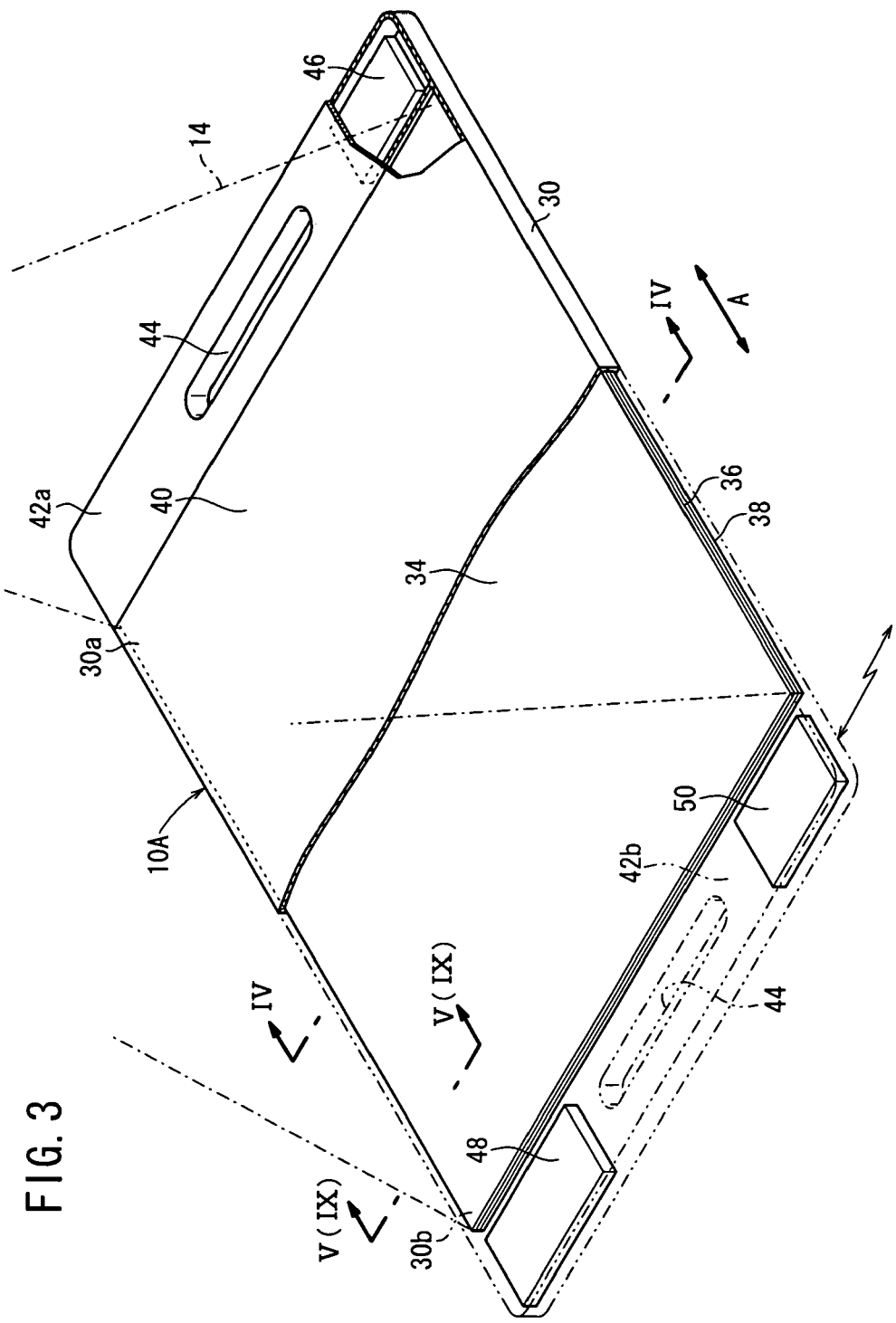
FIG. 3 is a perspective view, partially cut away, of the radiation detecting apparatus of FIG. 1.

As shown in FIG. 3, in the interior of the grips 42a, 42b there are accommodated a battery 46 serving as a power supply for the radiation detecting cassette 10A, a cassette controller 48 for controlling operation of the radiation detector 20 with electric power supplied from the battery 46, and a transceiver (wireless communication unit) 50 for sending and receiving signals including information of radiation 14 detected by the radiation detector 20 to and from the console 24. In greater detail, one of the grips 42a houses the battery 46 therein, whereas the other grip 42b houses the cassette controller 48 and the transceiver 50 therein.

So that the cassette controller 48 and the transceiver 50 are not damaged by irradiation from the radiation 14, preferably, lead plates or the like are arranged in the grips 42a, 42b at sides of the irradiated surface 40 of the screen 30. Further, the battery 46 supplies electrical power to the radiation detector 20 inside the radiation detecting cassette 10A, the cassette controller 48, and the transceiver 50.

Figure 5:
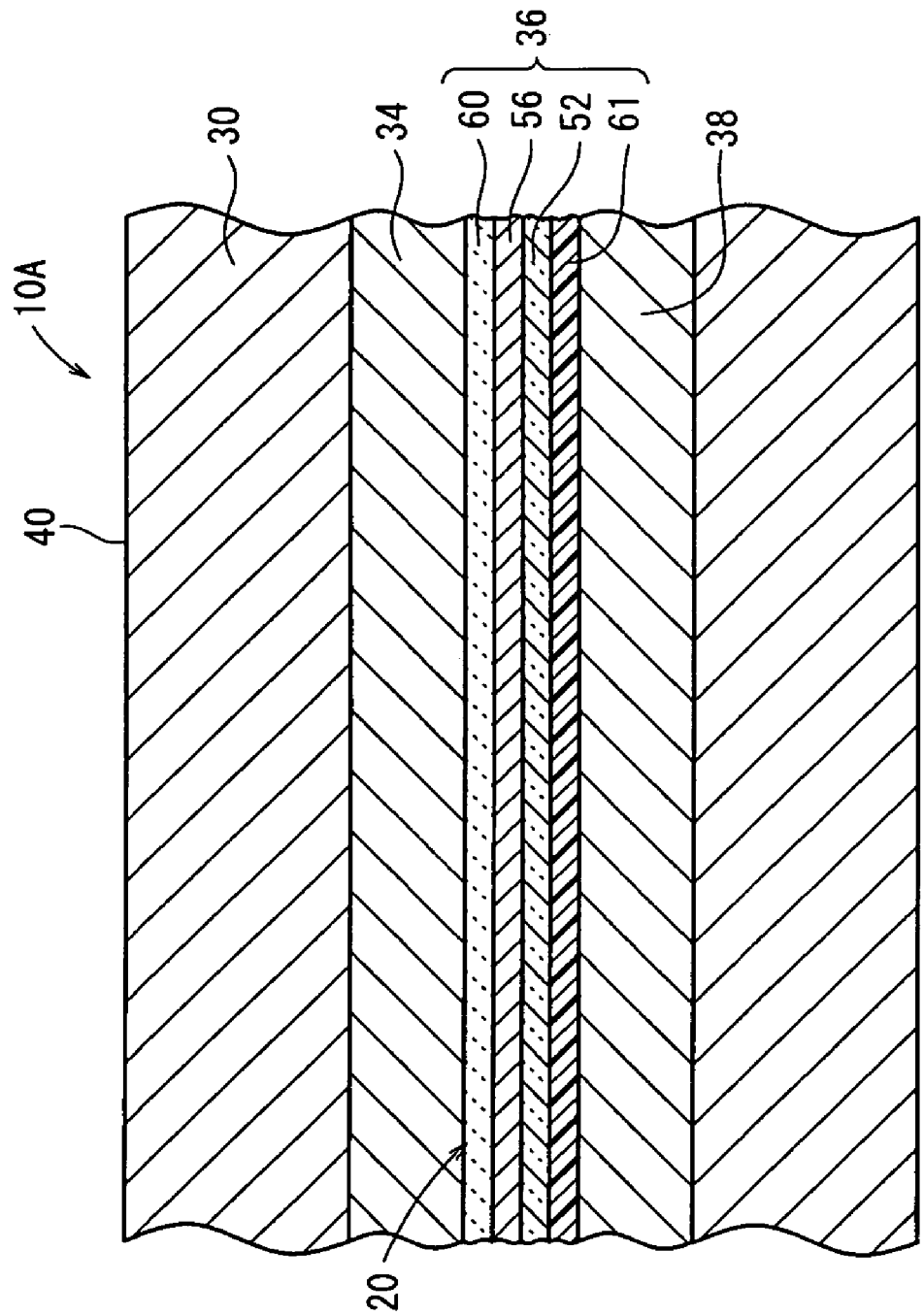
FIG. 5 is a cross-sectional view taken along line V-V of FIG. 3.

As shown in FIG. 5, the sensor substrate 36 is made up from a scintillator 52 made of a phosphor, such as GOS ($Gd_2O_2S$) or CsI:Tl or the like for converting radiation 14 that has passed through the patient 16 into visible light, a TFT layer 56 formed from an array of thin-film transistors (TFTs) (see FIG. 6), the TFT layer 56 being permeable to radiation 14 and visible light, and a photoelectric transducer layer 60 including solid-state detectors (hereinafter referred to as "pixels") 58 made of a material such as amorphous silicon (a-Si) or the like for converting the visible light into electric signals. The scintillator 52, the TFT layer 56 and the photoelectric transducer layer 60 are stacked in this order on a substrate 61.

The substrate 61 may be made of polyethylene terephthalate (PET), polyethylene naphthalate (PEN), polyimide (e.g., Kapton (registered trademark) of DuPont), polysulfone ether (PES), polycarbonate (PC), or the like, as disclosed in Japanese Laid-Open Patent Publication No. 2003-070776.

Figure 6:
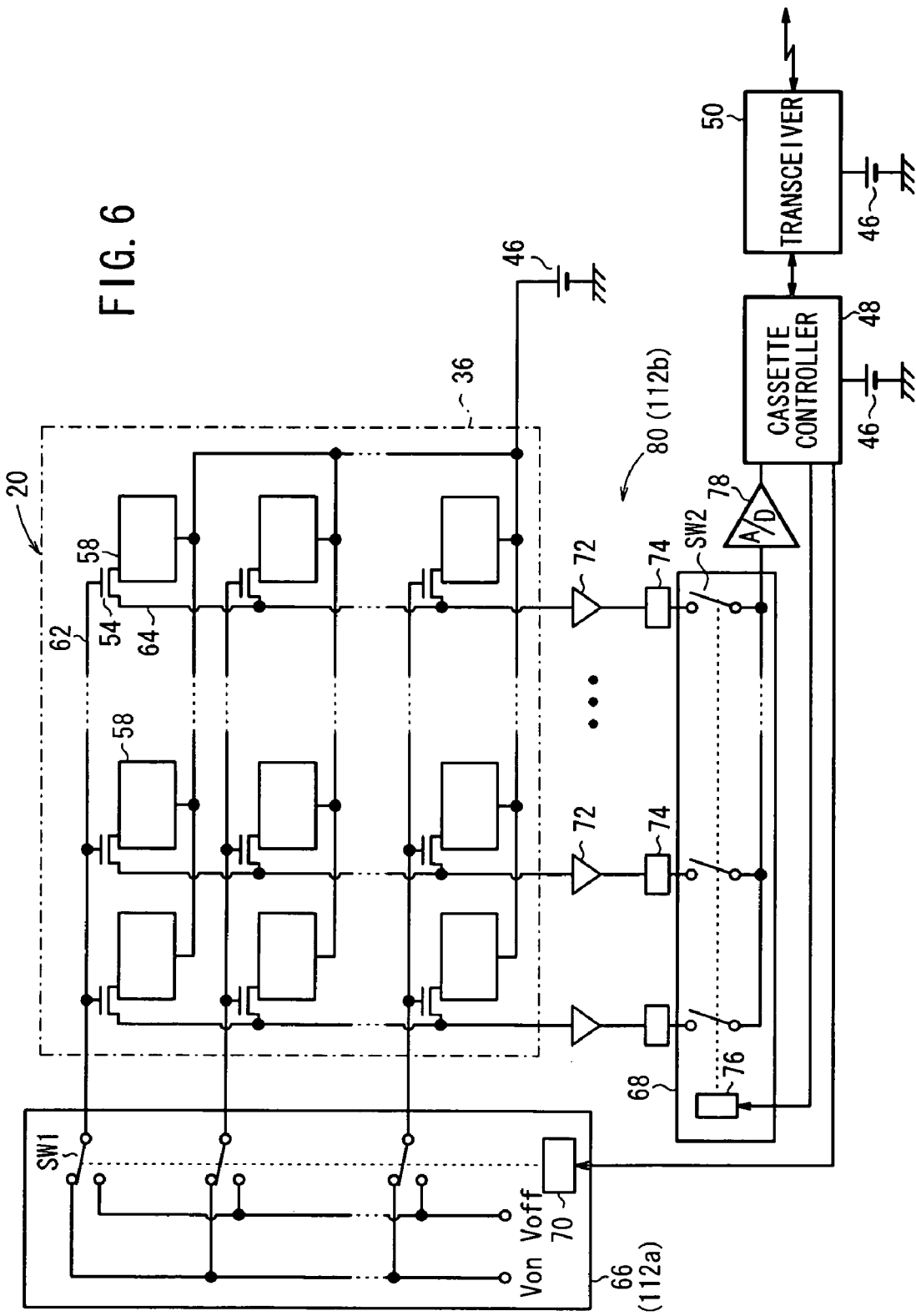
FIG. 6 is a block diagram of a circuit arrangement of the radiation detecting apparatus shown in FIG. 1.

As shown in FIG. 6, the radiation detector 20 comprises an array of thin-film transistors (TFTs) 54 arranged in rows and columns (the TFT layer 56), with the photoelectric transducer layer 60 (see FIG. 5), which is formed of the pixels 58 made of a material such as amorphous silicon (a-Si) or the like for converting visible light into electric signals, being disposed on the array of TFTs 54. In this case, the pixels 58 store the generated electric charges, which are generated when the visible light is converted into electric signals. Then, the TFTs 54 are sequentially turned on each row to read the electric charges from the pixels 58 as an image signal.

The TFTs 54 connected to the respective pixels 58 are connected to respective gate lines 62 extending parallel to the rows, and respective signal lines 64 extending parallel to the columns. The gate lines 62 are connected to a line scanning driver (driver) 66, and the signal lines 64 are connected to a multiplexer 68. The gate lines 62 are supplied with control signals Von, Voff for turning on and off the TFTs 54 along the rows from the line scanning driver 66. The line scanning driver 66 comprises a plurality of switches SW1 for switching between the gate lines 62, and an address decoder 70 for outputting a selection signal for selecting one of the switches SW1 at a time. The address decoder 70 is supplied with an address signal from the cassette controller 48.

The signal lines 64 are supplied with electric charges stored in the pixels 58 through the TFTs 54 arranged in the columns. Electric charges supplied to the signal lines 64 are amplified by amplifiers 72 connected respectively to the signal lines 64. The amplifiers 72 are connected through respective sample and hold circuits 74 to the multiplexer 68. The multiplexer 68 comprises a plurality of switches SW2 for successively switching between the signal lines 64, and an address decoder 76 for outputting a selection signal for selecting one of the switches SW2 at a time. The address decoder 76 is supplied with an address signal from the cassette controller 48. The multiplexer 68 has an output terminal connected to an A/D converter 78. A radiation image signal, which is generated by the multiplexer 68 based on electric charges from the sample and hold circuits 74, is converted by the A/D converter 78 into a digital image signal representing radiation image information, which is supplied to the cassette controller 48. The amplifiers 72, the sample and hold circuits 74, the multiplexer 68, and the A/D converter 78 constitute a reading circuit (reader) 80.

The TFTs 54, which function as switching devices, may be combined with another image capturing device, such as a CMOS (Complementary Metal-Oxide Semiconductor) image sensor or the like. Alternatively, the TFTs 54 may be replaced with a CCD (Charge-Coupled Device) image sensor for shifting and transferring electric charges with shift pulses corresponding to gate signals in the TFTs.

As shown in FIG. 1, the cassette controller 48 of the radiation detecting cassette 10A includes an address signal generator 82, an image memory 84, and a cassette ID memory 86.

The address signal generator 82 supplies address signals to the address decoder 70 of the line scanning driver 66, and to the address decoder 76 of the multiplexer 68 of the radiation detector 20. The image memory 84 stores the radiation image information detected by the radiation detector 20. The cassette ID memory 86 stores cassette ID information for identifying the radiation detecting cassette 10A.

The transceiver 50 transmits the cassette ID information stored in the cassette ID memory 86 and the radiation image information stored in the image memory 84 to the console 24 by way of wireless communications.

The radiation detecting cassette 10A and the radiation image capturing system 12A according to the first embodiment are basically constructed as described above. Operations of the radiation detecting cassette 10A and the radiation image capturing system 12A will be described below.

Patient information of the patient 16 to be imaged is registered in the console 24 in advance, prior to commencing an image capturing process. If a region to be imaged and an image capturing method are known beforehand, then such image capturing conditions also are registered in the console 24.

Figure 7:
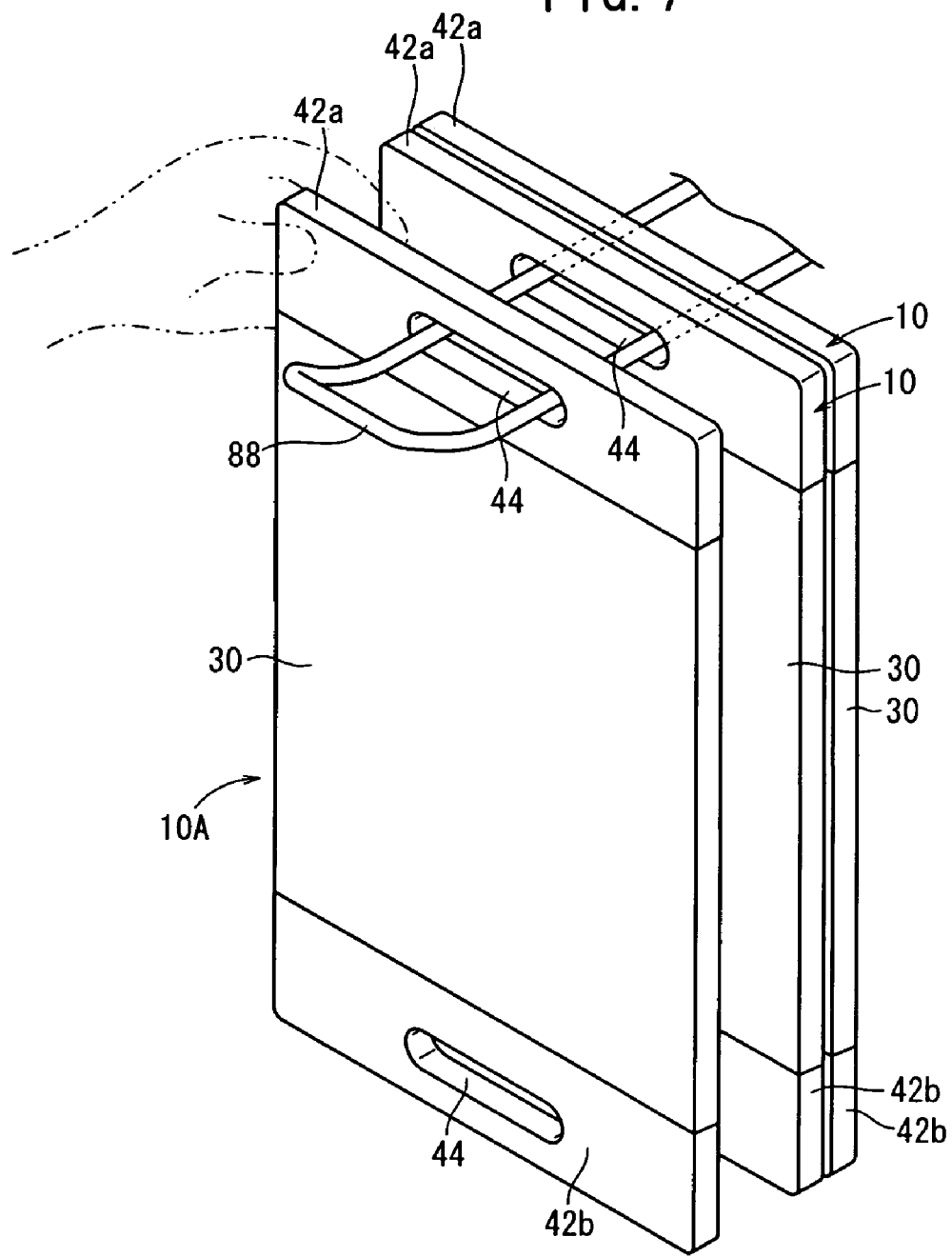
FIG. 7 is a perspective view showing a state in which the radiation detecting apparatus of FIG. 2 is hung on a hook.

In the event that capturing of radiation image information is performed in an operating room, when the doctor examines the patient 16, or when the doctor goes on rounds in the hospital, as shown in FIG. 7, one of the grips 42a of the radiation detecting cassette 10A, which is hung on a hook 88 in a storage box (not shown) through holes 44 in the grips 42a, 42b, is grasped and the radiation detecting cassette 10A is taken out. The radiation detecting cassette 10A is placed at a predetermined position between the patient 16 and a bed, for example, in a condition such that the irradiated surface 40 thereof faces toward the radiation source 18 (see FIG. 4).

At this time, by grasping the rigidly formed grip 42a (42b), handling of the radiation detecting cassette 10A equipped with the flexible screen 30 is facilitated, so that the radiation detecting cassette 10A can reliably and easily be moved to a predetermined position. Further, by inserting one's fingers through the holes 44 provided in the grips 42a, 42b and grasping the same, the radiation detecting cassette 10A can be gripped more reliably, thus reducing the possibility of dropping the radiation detecting cassette 10A.

Next, after the radiation source 18 has been moved into an appropriate position facing the radiation detecting cassette 10A, a doctor or radiological technician operates the image capturing switch of the radiation source 18 to perform capturing of the radiation image. When the image capturing switch is operated, the radiation source 18 sends a request to the console 24 to transmit the image capturing conditions by way of wireless communications. In response to this request, the console 24 transmits the image capturing conditions to the radiation source 18 concerning the region to be imaged of the patient 16. When the radiation source 18 receives the image capturing conditions, the radiation source 18 applies radiation 14 to the patient 16 at a predetermined dose according to the image capturing conditions.

Radiation 14 that has passed through the patient 16 is applied to the grid 34 of the radiation detecting cassette 10A, which removes scattered rays from the radiation 14. Then, the radiation 14 is applied to the radiation detector 20. The scintillator 52 of the radiation detector 20 emits visible light, at an intensity that depends on the intensity of the applied radiation 14. The pixels 58 of the photoelectric transducer layer 60 convert the visible light into electric signals and store the signals as electric charges. The stored electric charges, which represent radiation image information of the patient 16, are read from the pixels 58 according to address signals, which are supplied from the address signal generator 82 of the cassette controller 48 to the line scanning driver 66 and the multiplexer 68.

More specifically, in response to the address signals supplied from the address signal generator 82, the address decoder 70 of the line scanning driver 66 outputs a selection signal to select one of the switches SW1, which supplies the control signal Von to the gates of the TFTs 54, which are connected to the gate line 62 corresponding to the selected switch SW1. In response to the address signals supplied from the address signal generator 82, the address decoder 76 of the multiplexer 68 outputs a selection signal, so as to successively turn on the switches SW2 to switch between the signal lines 64, for thereby reading the electric charges stored in the pixels 58 connected to the selected gate line 62 through the signal lines 64.

The electric charges read from the pixels 58 connected to the selected gate line 62 of the radiation detector 20 are amplified by the respective amplifiers 72, sampled by the sample and hold circuits 74, and supplied to the multiplexer 68. Based on the supplied electric charges, the multiplexer 68 generates and supplies a radiation image signal to the A/D converter 78, which converts the radiation image signal into digital signals. Digital signals, which represent the radiation image information, are stored in the image memory 84 of the cassette controller 48.

Similarly, the address decoder 70 of the line scanning driver 66 successively turns on the switches SW1 to switch between the gate lines 62 according to the address signal supplied from the address signal generator 82. The electric charges stored in the pixels 58 connected to the successively selected gate lines 62 are read through the signal lines 64, and processed by the multiplexer 68 and the A/D converter 78 into digital signals, which are stored in the image memory 84 of the cassette controller 48.

The radiation image information stored in the image memory 84 is transmitted from the transceiver 50 to the console 24 by way of wireless communications. The console 24 performs predetermined image processing on the received radiation image information, and stores the processed radiation image information in a memory, in association with registered patient information of the patient 16. The processed radiation image information is transmitted from the console 24 to the display device 22, which displays a radiation image based on the radiation image information.

Additionally, when capturing of the radiation image is completed, the doctor or radiological technician grips the grips 42a, 42b of the radiation detecting cassette 10A, transports it again to the storage box, and stores the radiation detecting cassette 10A in a state whereby the hook 88 is inserted through the hole 44 of the grip 42a, and the radiation detecting cassette 10A is hung on the hook 88. In this case as well, the radiation detecting cassette 10A is moved easily and reliably from the bed into the storage box (not shown), and can be accommodated by hanging thereof on the hook 88 via the grip 42a (42b). At this time, the radiation detecting cassette 10A is stored such that one of the grips 42a hung on the hook 88 is arranged upwardly, whereas the other grip 42b hangs downwardly under the weight of the radiation detecting cassette 10A, and the screen 30 between the grips 42a, 42b is accommodated in a flat planar state without being curved (see FIG. 7). Stated otherwise, the radiation detecting cassette 10A is accommodated in a straight fashion and oriented vertically while hanging on the hook 88.

As described above, with the radiation detecting cassette 10A and radiation image capturing system 12A according to the first embodiment, a pair of grips 42a, 42b, which can be gripped by a doctor or radiological technician, are disposed on both ends 30a, 30b of the screen 30 constituting the radiation detecting cassette 10A. By forming the grips 42a, 42b as rigid bodies, which differ from the screen 30, even in the case of a flexible radiation detecting cassette 10A, the radiation detecting cassette 10A can be reliably grasped and easily moved to a predetermined position, without adversely affecting handling of the radiation detecting cassette 10A upon gripping thereof by the doctor or radiological technician.

Further, by providing holes 44 centrally in the grips 42a, 42b, the doctor or radiological technician can insert his or her hands through the holes 44 and more reliably grasp the grips 42a, 42b, so that accidental dropping of the radiation detecting cassette 10A is prevented.

Moreover, using the holes provided in the grips 42a, 42b, for example, by insertion over the hook 88, the flexible radiation detecting cassette 10A can be stored easily and safely in a non-flexed (unwarped) state.

Furthermore, since the radiation detector 20 includes the scintillator 52, the TFT layer 56, and the photoelectric transducer layer 60, which are arranged successively in this order on the substrate 61, or in other words, since the radiation detector 20 includes the photoelectric transducer layer 60, the TFT layer 56, and the scintillator 52, which are arranged successively in this order from the irradiated surface 40, visible light generated by the scintillator 52 can efficiently be converted into electric signals by the photoelectric transducer layer 60. As a result, the radiation detector 20 can produce high quality radiation image information.

Furthermore, with the radiation image capturing system 12A, since signals are sent and received by way of wireless communications between the console 24 and the radiation detecting cassette 10A, the radiation source 18, and the display device 22, no cables are required for transmitting and receiving signals therebetween, and hence cable-induced obstacles to operations performed by the doctor or radiological technician do not occur. Therefore, the doctor and the radiological technician are able to perform their work smoothly and efficiently.

According to the first embodiment, moreover, radiation image information is captured when the image capturing switch of the radiation source 18 is turned on by the doctor or radiological technician. However, radiation image information may be captured when the doctor or radiological technician operates the console 24.

Figure 4:
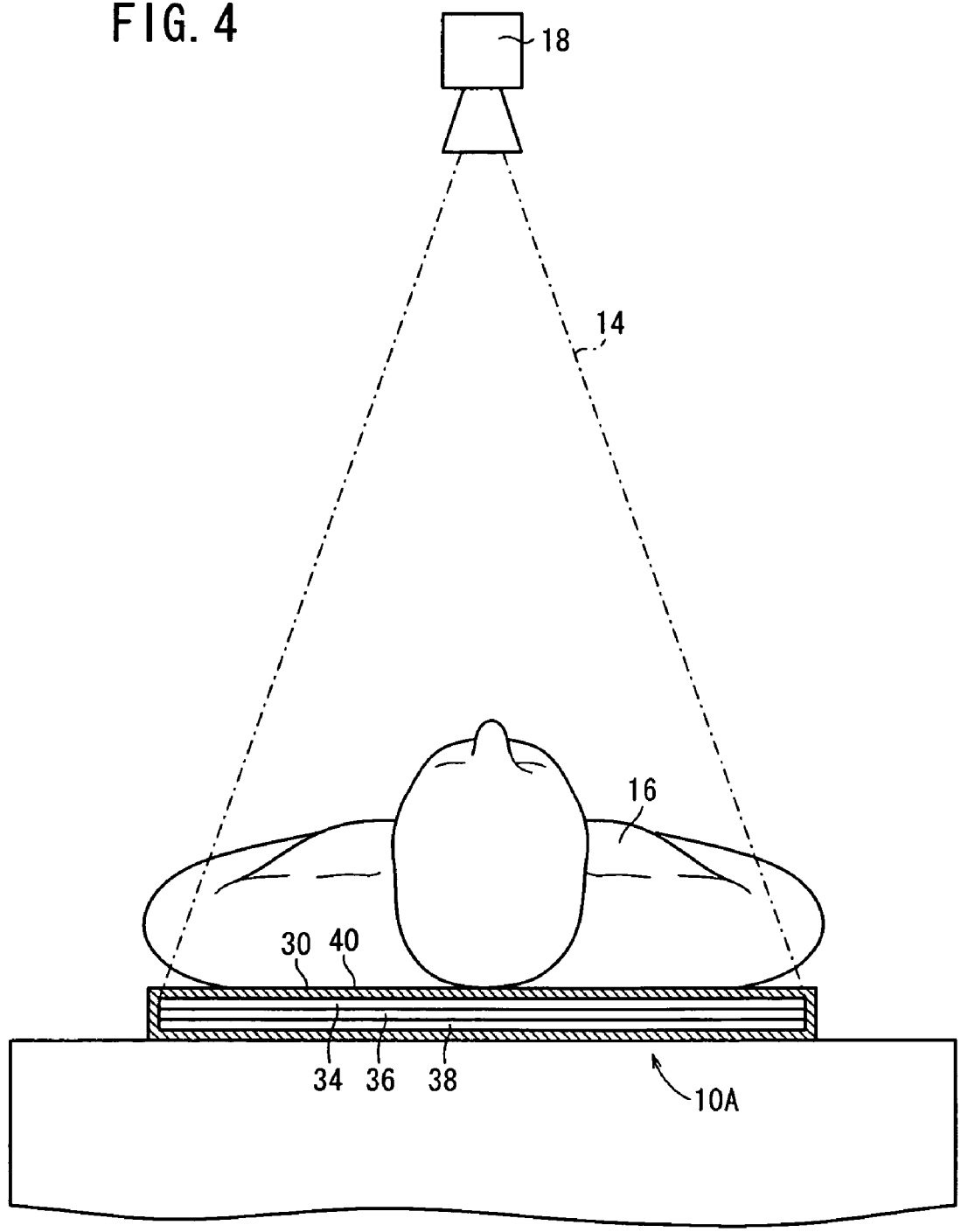
FIG. 4 is a cross-sectional view taken along line IV-IV of FIG. 3.
Figure 8:
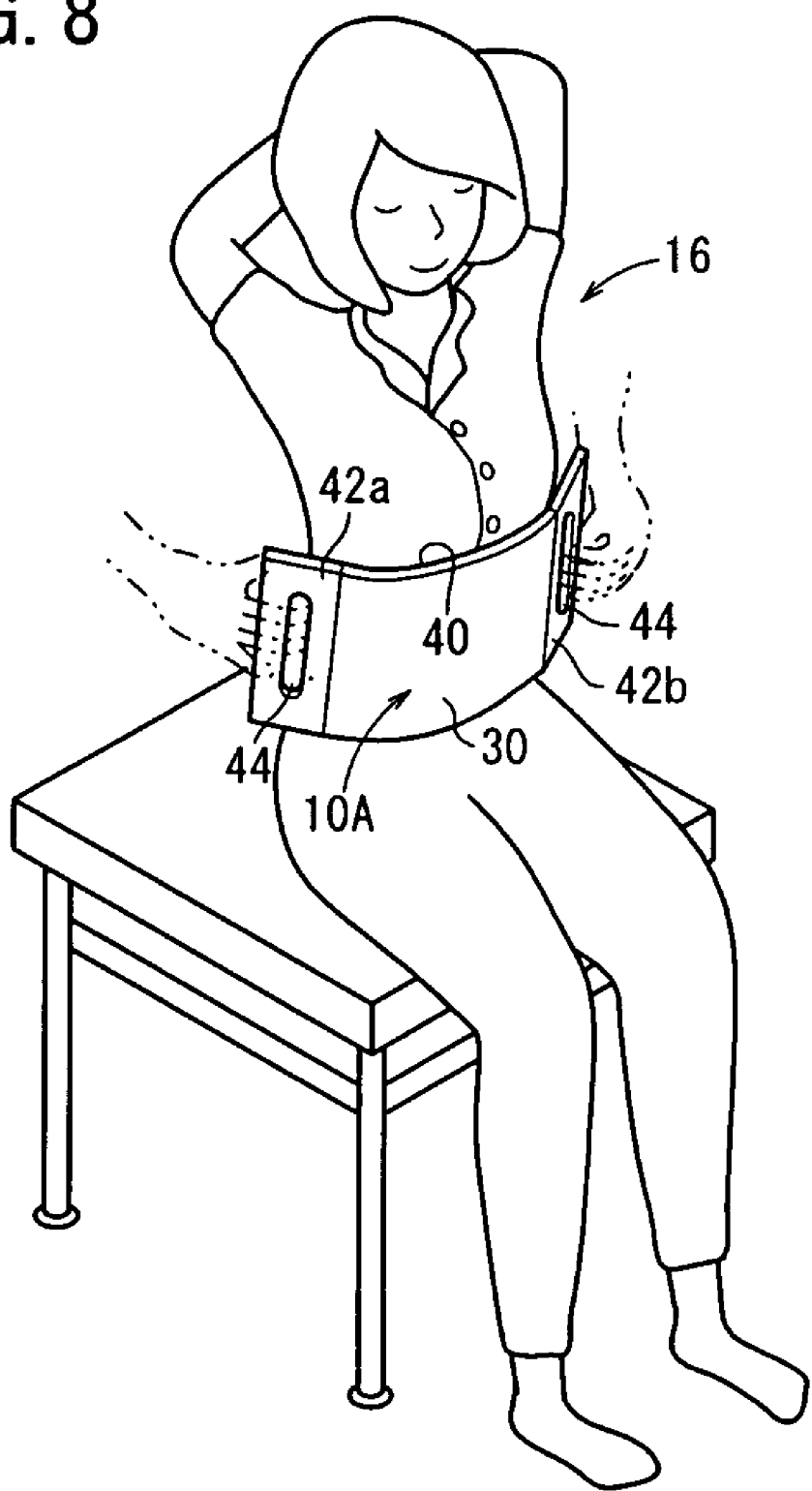
FIG. 8 is a perspective view showing a state in which the radiation detecting apparatus of FIG. 2 is placed in intimate contact against the abdomen of a patient.

Further, in the foregoing description, as shown in FIG. 4, a case has been explained in which the radiation detecting cassette 10A is positioned between the patient 16 and a bed. However, the invention is not limited to such an arrangement. For example, as shown in FIG. 8, the grips 42a, 42b of the radiation detecting cassette 10A may be gripped by a doctor or radiological technician and placed in direct contact against the abdomen of the patient 16, with the irradiated surface 40 facing toward the side of the patient 16. That is, the flexible screen 30 can be deformed to fit against the abdomen of the patient 16. In this case, radiation image is captured by applying radiation 14 from the radiation source 18, from a position on an opposite side from the radiation detecting cassette 10A sandwiching the patient 16 therebetween. As a result, using the flexible radiation detecting cassette 10A, an image can be captured suitably of a non-planar treatment region (e.g., the abdomen, flank, arm, etc.) of the patient 16.

Figure 9:
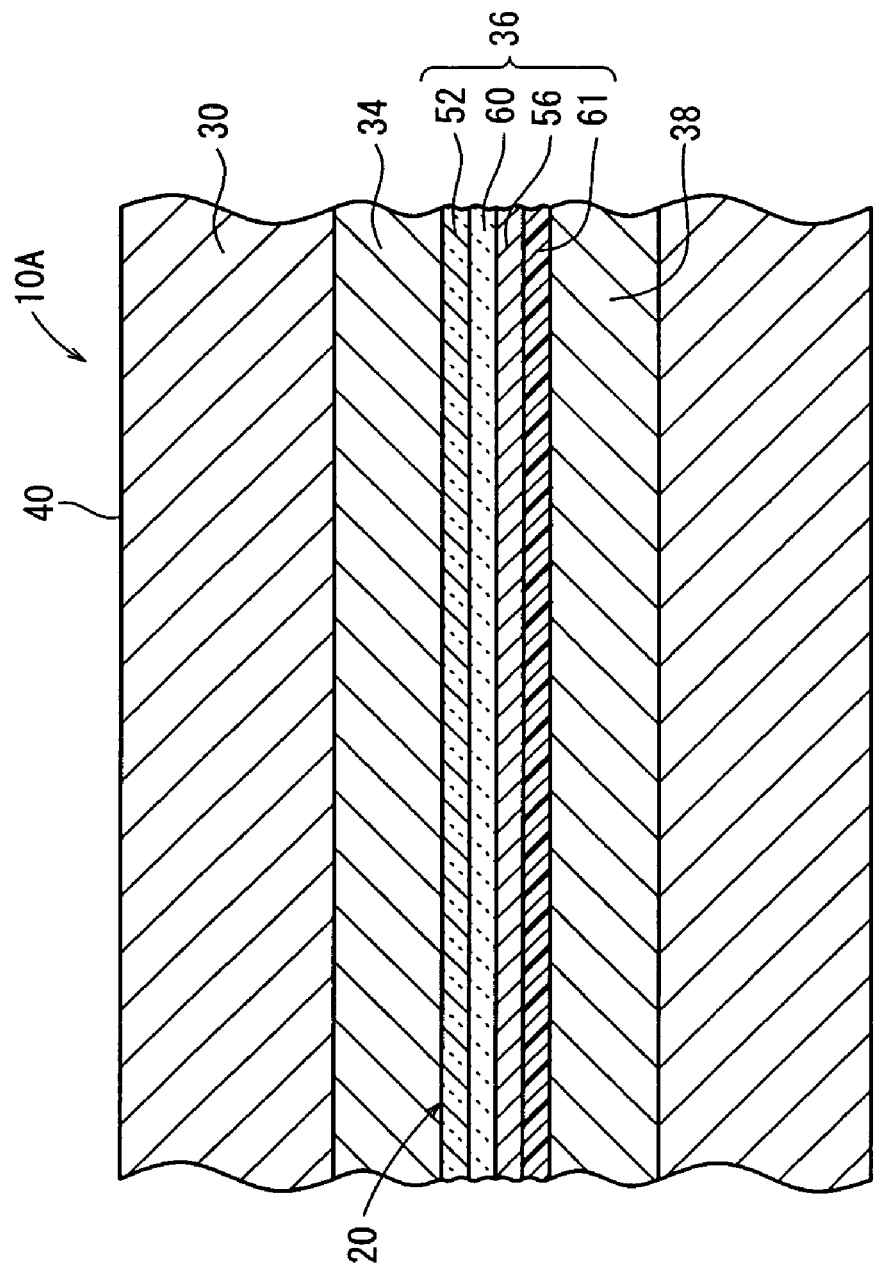
FIG. 9 is a cross sectional view taken along line IX-IX of FIG. 3.

The radiation detecting cassette 10A according to the first embodiment may also be constructed according to the arrangement or modification shown in FIG. 9. According to the arrangement or modification shown in FIG. 9, the TFT layer 56, the photoelectric transducer layer 60, and the scintillator 52 are stacked successively in this order from the substrate 61 toward the irradiated surface 40. With the modified radiation detecting cassette 10A, visible light converted by the scintillator 52 can be converted into electric signals by the photoelectric transducer layer 60. The modified radiation detecting cassette 10A can thus offer the same advantages as those described above.

According to the first embodiment, the principles of the present invention may be applied to a direct-conversion-type radiation detecting apparatus, wherein the dose of applied radiation 14 is converted directly into electric signals by a photoelectric transducer layer 60, which comprises solid-state detectors made of a material such as amorphous selenium (a-Se).

Further, according to the first embodiment, the radiation image capturing system 12A may employ a light read out type radiation detecting apparatus for acquiring radiation image information. Such a light read out type radiation detecting apparatus operates as follows. When radiation 14 is applied to a matrix of solid-state detecting devices, the solid-state detecting devices store an electrostatic latent image depending on the dose of applied radiation. For reading the stored electrostatic latent image, reading light is applied from a flexible organic EL (electroluminescent) panel or the like to a radiation detector in order to cause the radiation detector to generate an electric current representing the radiation image information. When erasing light is applied to the radiation detector, the radiation image information representing a residual electrostatic latent image is erased from the radiation detector, and the radiation detector can be reused (see Japanese Laid-Open Patent Publication No. 2000-105297).

Furthermore, according to the first embodiment, a stimulable phosphor panel for storing radiation energy representative of radiation image information, and thereafter emitting stimulated light representing the radiation image information upon exposure to stimulating light, may be used as a flexible radiation conversion panel.

When the radiation detecting cassette 10A is used in an operating room or the like, blood stains and other contaminants may be applied to the radiation detecting cassette 10A. The radiation detecting cassette 10A may comprise a water-resistant, sealed structure, so that the radiation detecting cassette 10A can be sterilized and cleaned to remove such blood stains and contaminants, thus enabling the radiation detecting cassette 10A to be used repeatedly.

Further, the radiation detecting cassette 10A and an external device (circuit) may communicate with each other by way of optical wireless communications using infrared rays or the like, rather than by means of usual wireless communications using radio waves.

Figure 10:
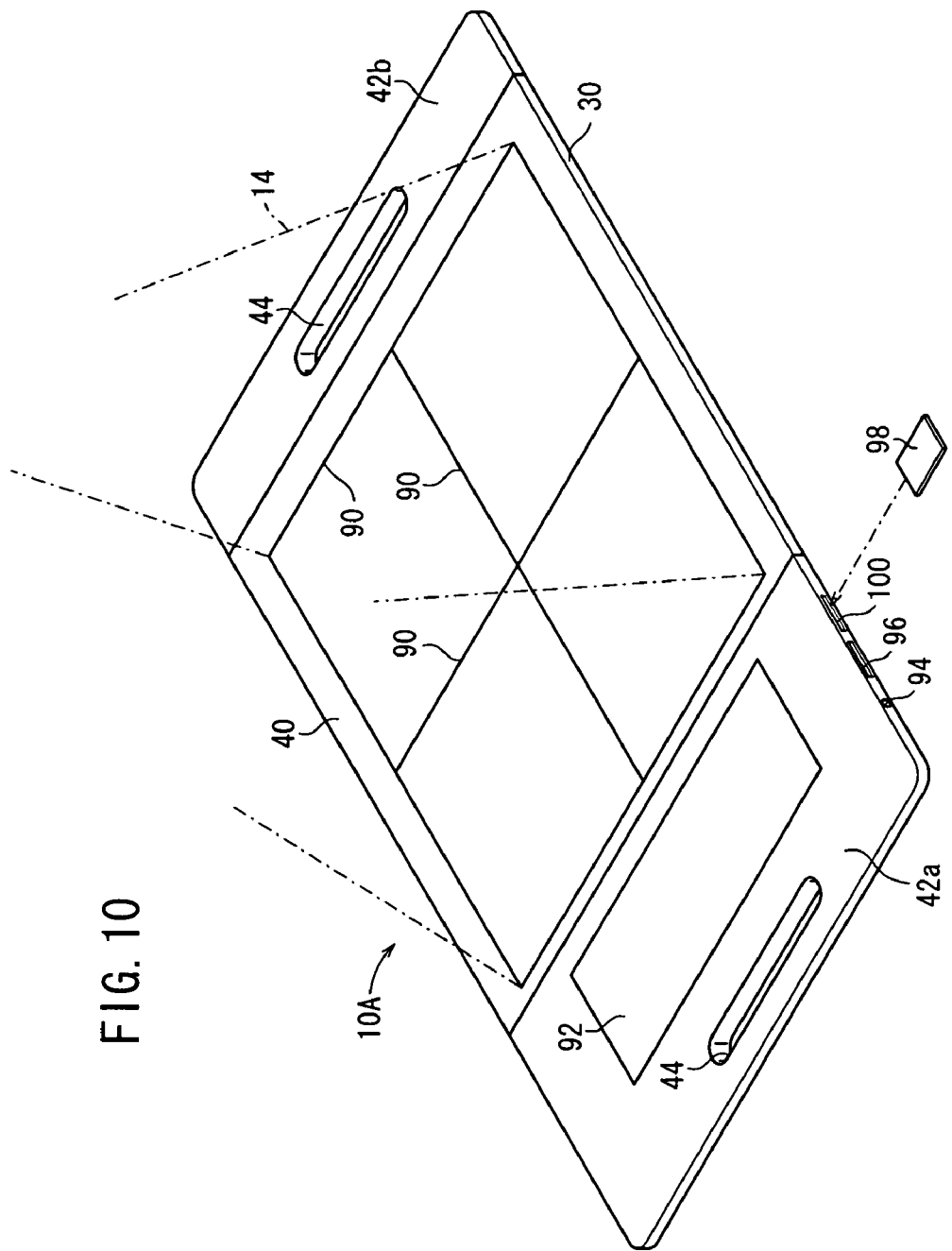
FIG. 10 is a perspective view showing another configuration of the radiation detecting apparatus according to the first embodiment.

FIG. 10 is a perspective view of another arrangement or modification of the radiation detecting cassette 10A according to the first embodiment.

The modified radiation detecting cassette 10A shown in FIG. 10 includes guide lines (markers) 90 drawn on the irradiated surface 40 of the screen 30, which serve as reference marks for an image capturing area and an image capturing position. Using such guide lines 90, the subject to be imaged, such as the patient 16, can be positioned with respect to the radiation detecting cassette 10A, and the range at which radiation 14 is to be applied to the radiation detecting cassette 10A can be determined, for thereby recording radiation image information within an appropriate image capturing area of the radiation detecting cassette 10A.

Further, on one of the grips 42a, which lies outside of the image capturing region of the radiation detecting cassette 10A, a display unit 92 is arranged for displaying various information concerning the radiation detecting cassette 10A. The display unit 92 displays ID information of the patient 16 whose radiation image information is to be recorded in the radiation detecting cassette 10A, the number of times that the radiation detecting cassette 10A has been used, an accumulated exposure dose, the charged state (remaining power level) of the battery 46 housed in the radiation detecting cassette 10A, image capturing conditions for the radiation image information, and a positioning image representing the patient 16 positioned with respect to the radiation detecting cassette 10A, etc. In this case as well, handling of the radiation detecting cassette 10A is facilitated when the grips 42a, 42b are gripped by holes 44 provided in each of the grips 42a, 42b. Also, the radiation detecting cassette 10A can be accommodated easily and safely by hanging the holes 44 onto a hook 88 or the like (see FIG. 7).

Further, the radiological technician, together with confirming the identity of the patient 16 according to the ID information displayed on the display unit 92, can confirm beforehand that the radiation detecting cassette 10A is in a usable condition, and can position the desired area to be imaged of the patient 16 with respect to the radiation detecting cassette 10A based on the displayed positioning image, so as to be capable of capturing optimum radiation image information.

The grip 42a suitably has an input terminal 94 for connection to an AC adapter, a USB (Universal Serial Bus) terminal 96, and a card slot 100 for receiving a memory card 98 therein.

When the charge on the battery 46 housed in the radiation detecting cassette 10A is low, or when there is not enough time to charge the battery 46, an AC adapter is connected to the input terminal 94, so as to supply electric power from an external source for thereby making the radiation detecting cassette 10A immediately usable.

The USB terminal 96 or the card slot 100 can be used when the radiation detecting cassette 10A is unable to send and receive information to and from an external device, such as the console 24 or the like, by way of wireless communications. More specifically, when a USB cable connected to the external device is connected to the USB terminal 96, the radiation detecting cassette 10A can send and receive information to and from the external device by way of wired communications through the USB terminal 96 and the USB cable. Alternatively, the memory card 98 can be inserted into the card slot 100, whereby necessary information from the radiation detecting cassette 10A is recorded in the memory card 98. Thereafter, the memory card 98 is disconnected and connected to the external device in order to send the recorded information from the memory card 98 to the external device.

Figure 11:
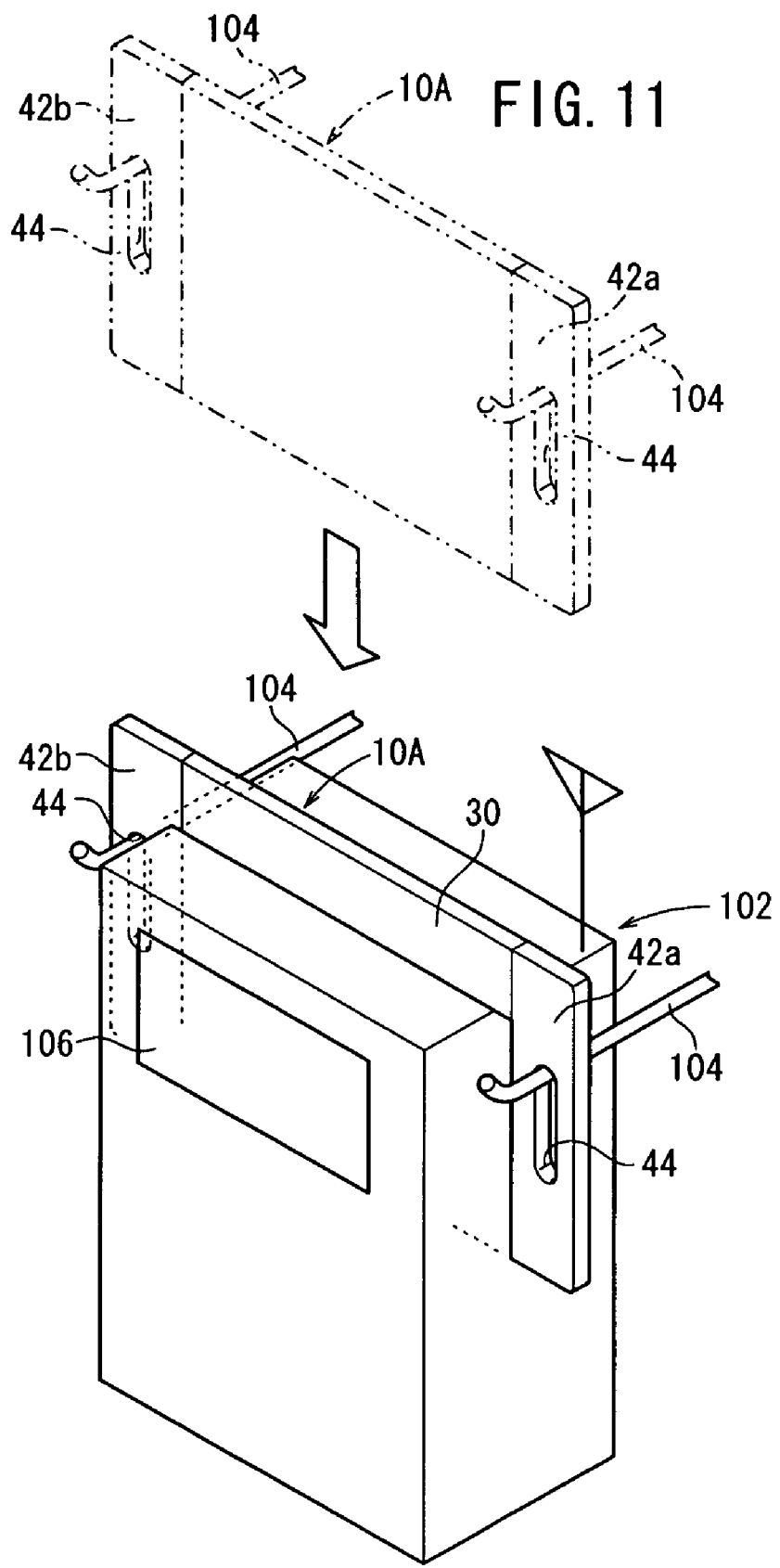
FIG. 11 is a perspective view of a cradle through which charging is performed with respect to the radiation detecting apparatus according to the first embodiment.

FIG. 11 shows a cradle 102 for receiving the radiation detecting cassette 10A therein and for charging the battery 46 housed in the radiation detecting cassette 10A. Preferably, the cradle 102 is positioned in an operating room or in another desired location in the hospital. In this case, the radiation detecting cassette 10A is arranged with the irradiated surface 40 thereof substantially vertical and the grips 42a, 42b substantially horizontal, and is inserted into the cradle 102 in a state where the holes 44 of the grips 42a, 42b are supported respectively on hooks 104.

The cradle 102 is not only capable of charging the battery 46, but may also have a wireless or wired communication function to send and receive necessary information to and from an external device, such as the RIS 26, the HIS 28, the console 24, or the like. The sent and received information may include radiation image information recorded in the radiation detecting cassette 10A, which is being charged in the cradle 102.

The cradle 102 may have a display unit 106 for displaying the charged state of the radiation detecting cassette 10A, as well as other necessary information including radiation image information acquired from the radiation detecting cassette 10A.

Further, a plurality of cradles 102 may be connected to a network, and the charged states of the radiation detecting cassettes 10A being charged in the respective cradles 102 can be retrieved through the network, so that the user can confirm and identify the locations of usable radiation detecting cassettes 10A, which are sufficiently charged, based on the retrieved charged states.

A radiation detecting apparatus (radiation detecting cassette) 10B according to a second embodiment of the present invention, and a radiation image capturing system 12B incorporating the radiation detecting cassette 10B therein, will be described below with reference to FIGS. 12 through 19.

Those parts of the radiation detecting cassette 10B and the radiation image capturing system 12B, which are identical to those of the radiation detecting cassette 10A and the radiation image capturing system 12A (see FIGS. 1 through 11), are denoted by identical reference characters, and such features will not be described in detail below. This also holds true for the other embodiments.

The radiation detecting cassette 10B and the radiation image capturing system 12B according to the second embodiment differ from the radiation detecting cassette 10A and the radiation image capturing system 12A of the first embodiment in that, in the interior of the screen 30, shape-memory members 110a, 110b are disposed on respective sides of the grid 34, the sensor substrate 36 and the lead sheet 38, in surrounding fashion to the grid 34, the sensor substrate 36 and the lead sheet 38. Furthermore, the battery 46, the cassette controller 48, the transceiver 50, driving circuit ICs (drivers) 112a that function as the line scanning driver 66 (see FIG. 6), and reading circuit ICs (readers) 112b that function as the reading circuit 80 are arranged on respective sides of the grid 34, the sensor substrate 36 and the lead sheet 38, while being sandwiched from above and below by the shape-memory members 110a, 110b.

More specifically, if the radiation detecting cassette 10B and the radiation image capturing system 12B according to the second embodiment were represented as a block diagram, the basic features thereof are the same as those of the radiation detecting cassette 10A and the radiation image capturing system 12A according to the first embodiment, as shown in FIG. 1. On the other hand, the second embodiment differs from the radiation detecting cassette 10A and the radiation image capturing system 12A of the first embodiment in respect to the positional arrangement of the respective structural elements thereof contained within the interior of the screen 30.

Basic differences between the radiation detecting cassette 10B and the radiation image capturing system 12B according to the second embodiment and the radiation detecting cassette 10A and the radiation image capturing system 12A according to the first embodiment have been described in outline form above. Next, specific structural features of the radiation detecting cassette 10B and the radiation image capturing system 12B according to the second embodiment shall be explained below in greater detail.

In the sheet-like radiation detecting cassette 10B shown in FIGS. 12 through 16B, the screen 30 which serves as a casing made of a material permeable to radiation 14 is flexible. At a time when radiation 14 is not applied with respect to the patient 16 (when an image is not being captured), the screen 30 can be wound in a rolled-up shape and stored in a non-illustrated storage box or the like. On the other hand, when radiation 14 is applied with respect to the patient 16 (during image capturing), the screen 30 is unrolled and laid out in a flat form with respect to the patient 16 by means of the shape-memory members 110a, 110b (see FIGS. 12, 14 and 16B).

In the interior of the screen 30, the shape-memory members 110a, 110b are disposed sequentially with respect to the irradiated surface 40 on side portions of the grid 34, the sensor substrate 36 and the lead sheet 38, while surrounding the grid 34, the sensor substrate 36, and the lead sheet 38. Above the shape-memory member 110b, circuit boards 114a, 114b are disposed at predetermined intervals along side portions of the sensor substrate 36. The driving circuit ICs 112a and the reading circuit ICs 112b, which make up the radiation detector 20, are disposed respectively above the circuit boards 114a, 114b. The driving circuit ICs 112a function as the line scanning driver 66 (see FIG. 6) for driving the TFTs 54 of the sensor substrate 36, whereas the reading circuit ICs 112b function as a reading circuit 80 for causing the TFTs 54 to be driven by the driving circuit ICs 112a and reading out the electrical charges stored in the pixels 58 as image signals. In addition, above the shape-memory member 110b, the battery 46, the cassette controller 48 and the transceiver 50 are arranged.

Figure 12:
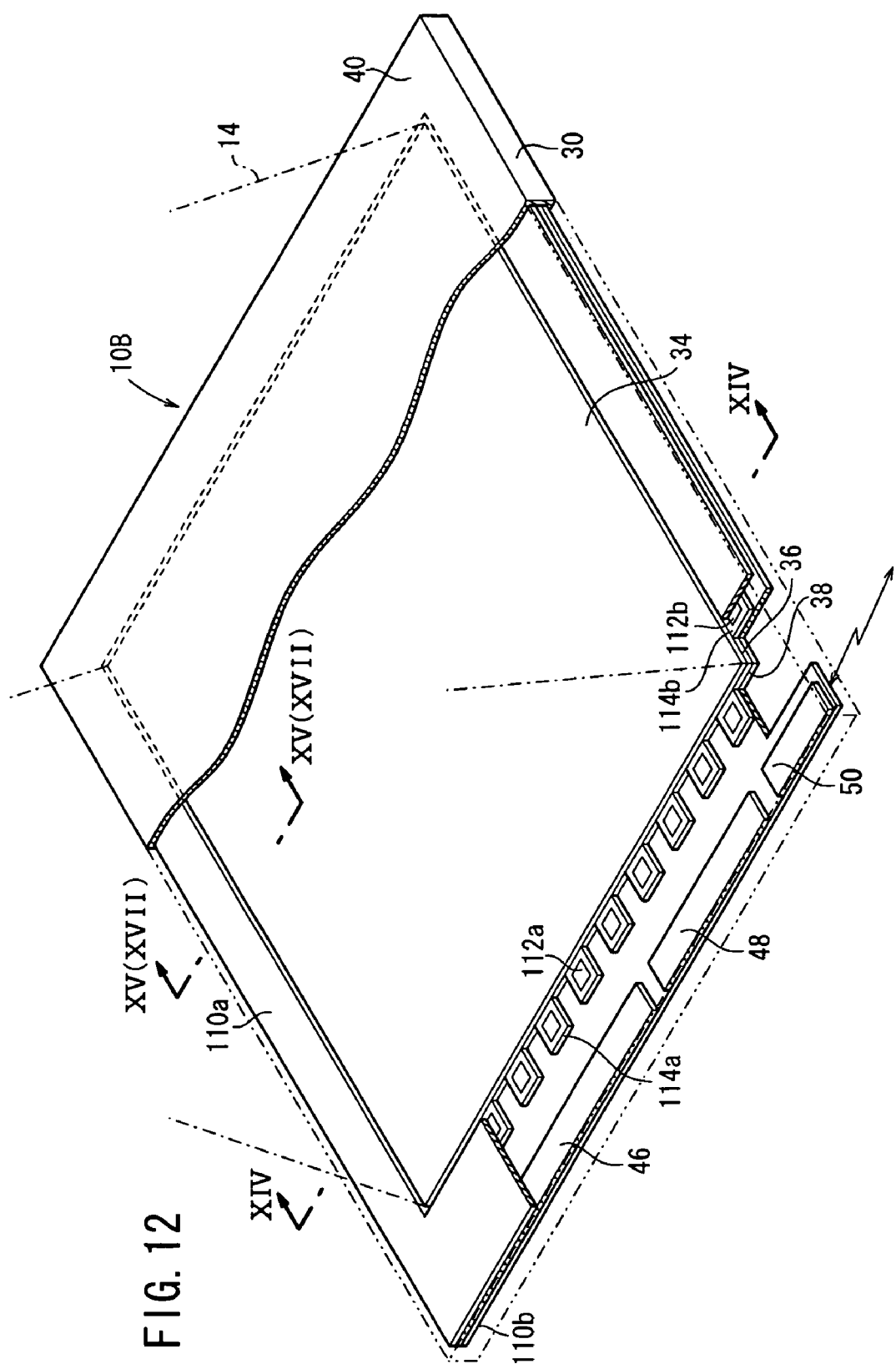
FIG. 12 is a perspective view of a radiation detecting apparatus according to a second embodiment of the present invention.
Figure 13:
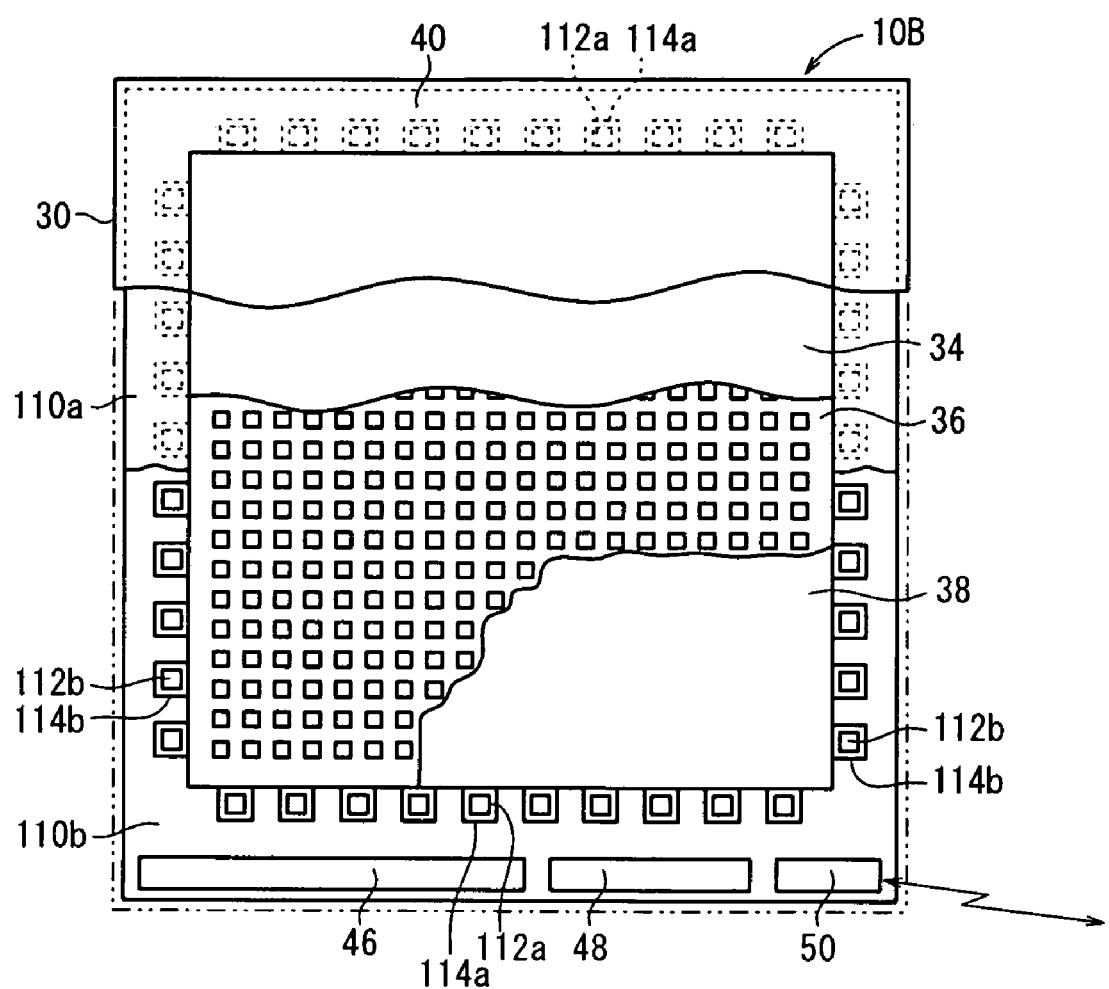
FIG. 13 is a plan view, with partial omission, of the radiation detecting apparatus of FIG. 12.
Figure 14:
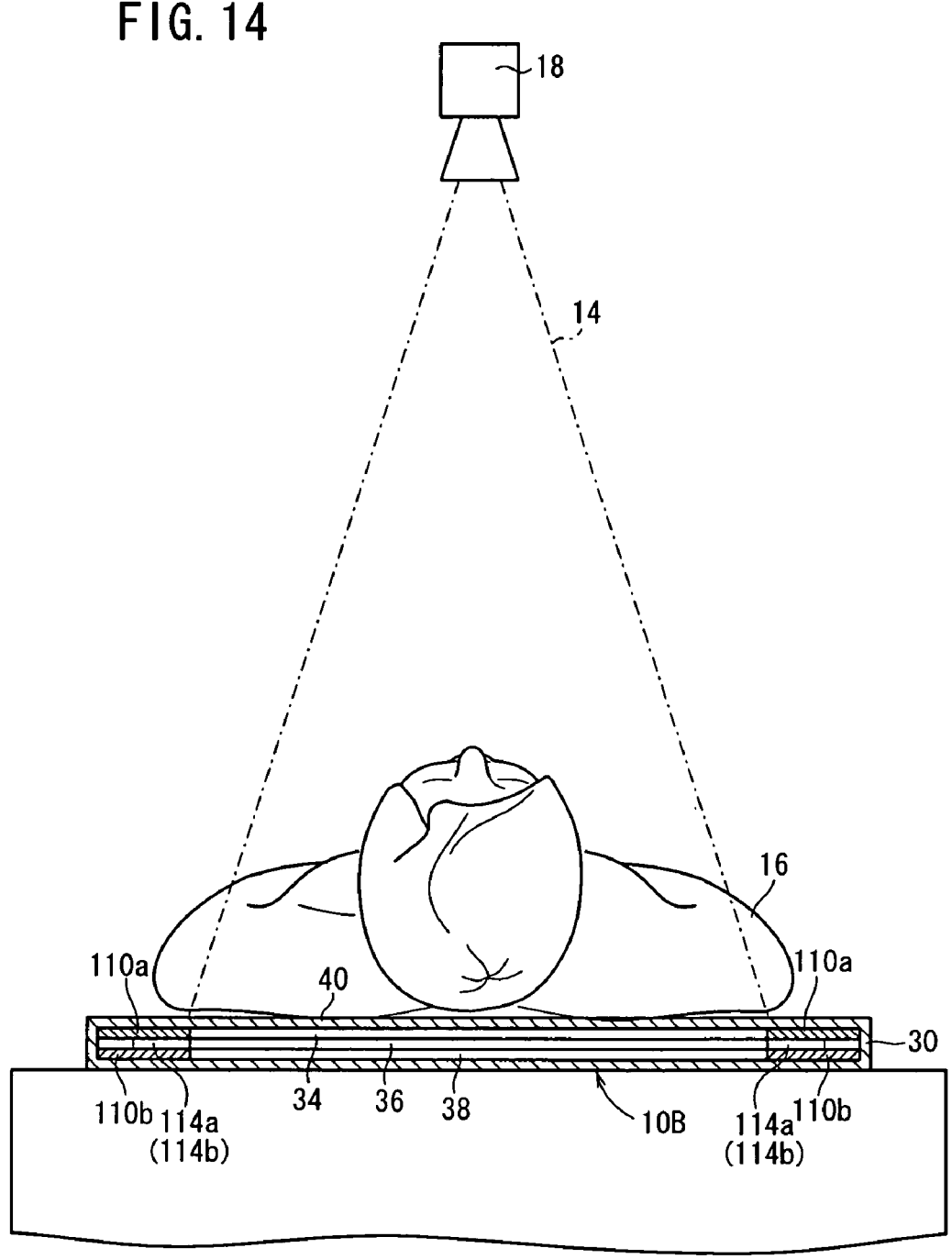
FIG. 14 is a cross-sectional view taken along line XIV-XIV of FIG. 12.
Figure 15:
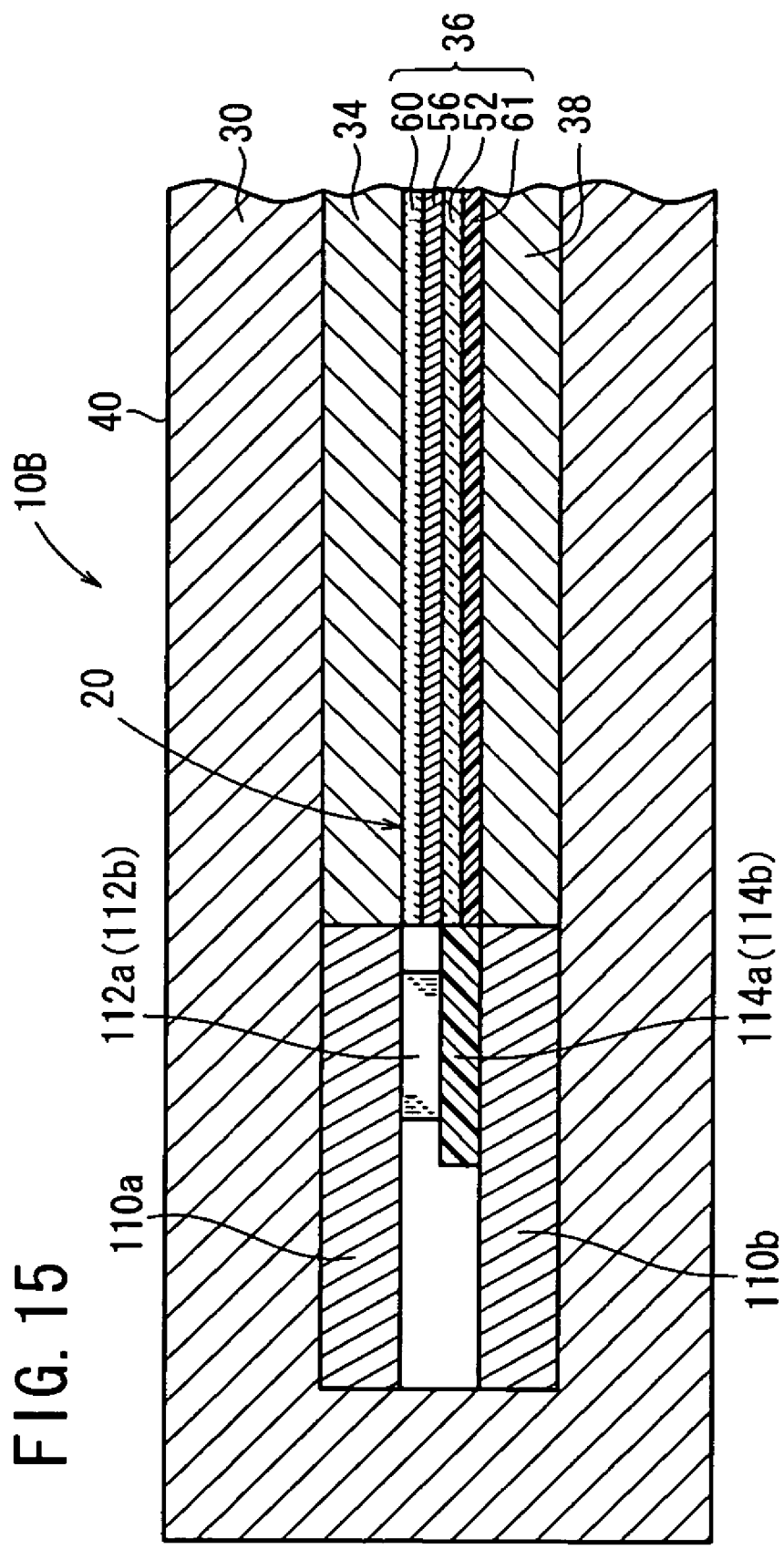
FIG. 15 is a cross-sectional view taken along line XV-XV of FIG. 12.
Figure 16A:
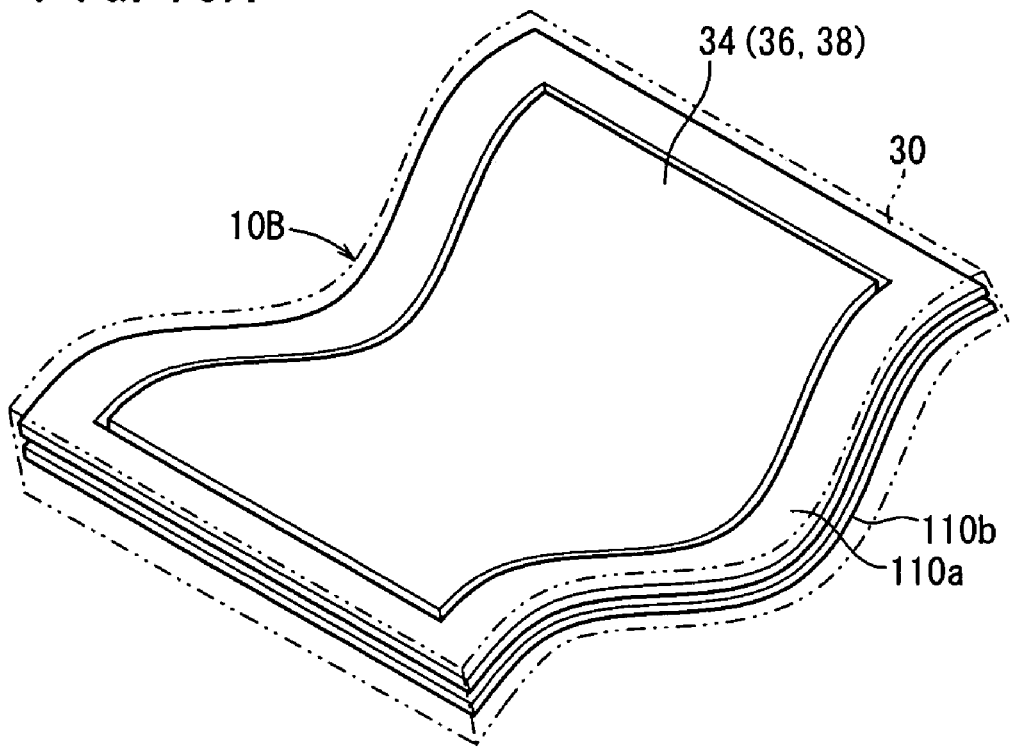
FIG. 16A is a schematic perspective view of a flexible radiation detecting apparatus.
Figure 16B:
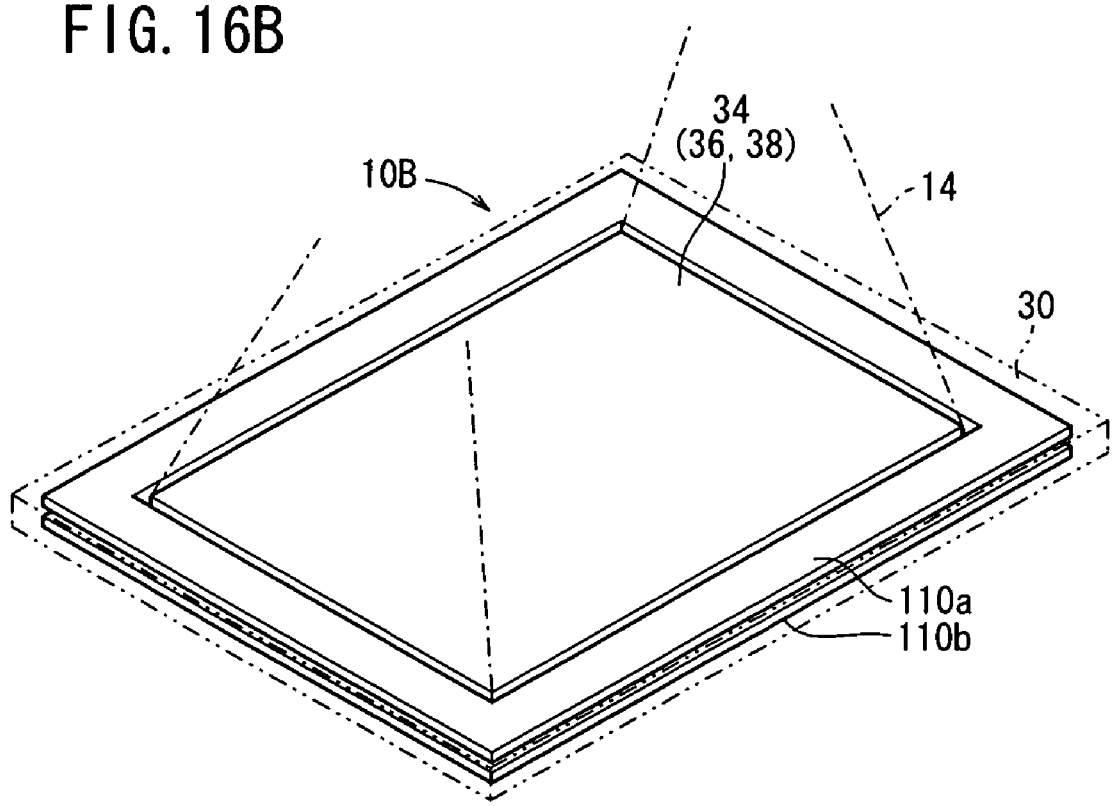
FIG. 16B is a schematic perspective view in which the radiation detecting apparatus is laid out in a planar shape.

As shown in FIGS. 12, 14 and 15, the driving circuit ICs 112a, the reading circuit ICs 112b, the battery 46, the cassette controller 48 and the transceiver 50 are accommodated inside the screen 30 in a state of being sandwiched from above and below by the shape-memory members 110a, 110b. In this case, the majority of heat which is generated upon operation of the driving circuit ICs 112a, the reading circuit ICs 112b, the battery 46, the cassette controller 48, and the transceiver 50 is transferred in upper and lower directions from top and bottom surfaces, respectively, of the driving circuit ICs 112a, the reading circuit ICs 112b, the battery 46, the cassette controller 48, and the transceiver 50, whereby such heat is dissipated to the exterior. Accordingly, the shape-memory members 110a, 110b are disposed along the heat radiating line of the driving circuit ICs 112a, the reading circuit ICs 112b, the battery 46, the cassette controller 48, and the transceiver 50.

Herein, when the transformation temperature of the shape-memory material constituting the shape-memory members 110a, 110b is somewhat lower than the temperature of the heat radiating line (the temperature at the location where the shape-memory members 110a, 110b are disposed) upon operation of the driving circuit ICs 112a, the reading circuit ICs 112b, the battery 46, the cassette controller 48, and the transceiver 50 (i.e., the transformation temperature is a certain temperature higher than ordinary temperature), since the temperature of the shape-member members 110a, 110b at times when the driving circuit ICs 112a, the reading circuit ICs 112b, the battery 46, the cassette controller 48, and the transceiver 50 are not operated is lower than the aforementioned transformation temperature, the shape-memory members 110a, 110b are capable of assuming any optional flexible shape (for example, the corrugated shaped shown schematically in FIG. 16A), and the screen 30 as well can assume any optional shape.

On the other hand, when the driving circuit ICs 112a, the reading circuit ICs 112b, the battery 46, the cassette controller 48, and the transceiver 50 are operated (e.g., when radiation is applied with respect to the patient 16 to capture a radiation image), because the temperature of the shape-memory members 110a, 110b becomes greater than the transformation temperature due to heat radiation of the driving circuit ICs 112a, the reading circuit ICs 112b, the battery 46, the cassette controller 48, and the transceiver 50, the shape-memory members 110a, 110b are restored to their original shape (i.e., the shaped shown schematically by FIG. 16B, or the shape of the shape-memory members 110a, 110b before a predetermined shape-memory process is performed), and the screen 30 maintains a flat planar shape corresponding to the original shape.

In order to instigate the aforementioned shape-memory effect, the shape-memory members 110a, 110b preferably are formed from shape-memory materials, and more specifically, the below-described shape-memory alloys or shape-memory resins, having a transformation temperature which is somewhat lower than the heat radiating line temperature (e.g., ≧50° C.) of the driving circuit ICs 112a, the reading circuit ICs 112b, the battery 46, the cassette controller 48, and the transceiver 50.

More specifically, in the case that the shape-memory members 110a, 110b are made from a shape-memory alloy, the shape-memory alloy preferably is a Ni—Ti alloy.

Further, in the case that the shape-memory members 110a, 110b are made from a shape-memory resin, the shape-memory resin preferably is any of the following: (1) a shape-memory resin made from polynorbornene manufactured by Zeon Corporation, trans-1,4-polyisoprene manufactured by Kuraray Co., Ltd., styrene/butadiene copolymer manufactured by Asahi Kasei Corporation, or a synthetic resin containing polyurethane or the like manufactured by Mitsubishi Heavy Industries, Ltd., (2) a thermoplastic shape-memory polymer of polynorbornene, styrene-butadiene copolymer, polyurethane, polyester, acrylic resin, or polyolefin, etc., or (3) an IPN (interpenetrating polymer network) type shape-memory polymer formed by interlacing styrene polymer and acrylic polymer, acrylic polymer and styrene polymer, or fluorine-containing polymer and acrylic polymer.

The radiation detecting cassette 10B and the radiation image capturing system 12B according to the second embodiment are basically constructed as described above. Next, operations of the radiation detecting cassette 10B and the radiation image capturing system 12B will be described below.

For capturing radiation image information when the doctor performs a surgical operation in an operating room, when the doctor examines the patient, or when the doctor goes on rounds in the hospital, after patient information and the image capturing conditions have been registered, the doctor or a radiological technician removes a rolled radiation detecting cassette 10B from a storage box (not shown) and positions the radiation detecting cassette 10B at a predetermined position between the patient 16 and a bed, for example, in a condition such that the irradiated surface 40 thereof faces toward the radiation source 18.

Next, when the doctor or radiological technician operates the power switch of the radiation detecting cassette 10B, supply of electrical power is initiated from the battery 46 to the radiation detector 20, the cassette controller 48 and the transceiver 50, whereupon operation of the driving circuit ICs 112a, the reading circuit ICs 112b, the cassette controller 48 and the transceiver 50 is initiated. In this case, heat generated by operation of the driving circuit ICs 112a, the reading circuit ICs 112b, the battery 46, the cassette controller 48 and the transceiver 50 is radiated in upward and downward directions in FIGS. 12, 14 and 15. Therefore, when the temperature of the shape-memory members 110a, 110b due to such radiant heat exceeds the transformation temperature, the shape-memory members 110a, 110b change from the flexible optional shape (see FIG. 16A) to the original shape prior to shape-memory processing thereof (see FIG. 16B). As a result, the screen 30, as well as the grid 34, the sensor substrate 36 and the lead sheet 38 embedded within the screen 30, are maintained in a flat planar shape.

In this manner, in a condition where the screen 30 is maintained in a flat shape, after the radiation source 18 has been suitably moved to a position confronting the radiation detecting cassette 10B, and when the doctor or radiological technician operates the image capturing switch of the radiation source 18, a radiation image of the patient 16 is taken, in the same manner as the first embodiment.

After a radiation image of the patient 16 has been captured, when the doctor or radiological technician turns off the power switch, supply of electrical power from the battery 46 to the radiation detector 20, the cassette controller 48 and the transceiver 50 is halted, and operations of the driving circuit ICs 112a, the reading circuit ICs 112b, the cassette controller 48 and the transceiver 50 are stopped. Owing thereto, radiation of heat from the driving circuit ICs 112a, the reading circuit ICs 112b, the battery 46, the cassette controller 48 and the transceiver 50 also stops, and when the temperature of the shape-memory members 110a, 110b falls below the transformation temperature, the shape-memory members 110a, 110b can be changed from the original shape (see FIG. 16B) into any flexible optional shape (see FIG. 16A). Consequently, the doctor or radiological technician can wind up the screen 30 in a rolled shape, and the screen 30 can be accommodated in a storage box or the like.

As described above, in accordance with the radiation detecting cassette 10B and the radiation image capturing system 12B of the second embodiment, by means of the shape-memory members 110a, 110b, a flexible sensor substrate 36 (irradiated surface 40 or image capturing surface of the radiation detector 20) can be maintained in a flat planar shape with respect to the patient 16. Therefore, the sensor substrate 36 can easily be made to assume a planar shape.

Further, since the shape-memory members 110a, 110b are arranged alongside the grid 34, the sensor substrate 36 and the lead sheet 38, and act to maintain the grid 34, the sensor substrate 36 and the lead sheet 38 in a planar shape when radiation 14 is applied (i.e., during image capturing), the shape-memory members 110a, 110b reliably prevent any hindrance to application of radiation 14 with respect to the sensor substrate 36.

Furthermore, because the shape-memory members 110a, 110b are disposed in close proximity to the driving circuit ICs 112a and the reading circuit ICs 112b, when the temperature of the shape-memory members 110a, 110b exceeds the transformation temperature of the shape-memory material due to radiant heat from the driving circuit ICs 112a and the reading circuit ICs 112b, the shape-memory members 110a, 110b are restored to their original shape (the shape thereof before shape-memory processing is effected thereon), and as a result, the grid 34, the sensor substrate 36 and the lead sheet 38 can easily and effectively be restored to a planar shape.

Still further, because the shape-memory members 110a, 110b are disposed in close proximity to the transceiver 50 which is capable of wireless communications with the console 24, the cassette controller 48 for controlling the radiation detector 20, and the battery 46 for energizing the radiation detector 20, the cassette controller 48 and the transceiver 50, the shape-memory members 110a, 110b are made to assume their original shapes due to heat generated upon operation of the driving circuit ICs 112a and the reading circuit ICs 112b, as well as due to heat generated upon operation of the transceiver 50, the cassette controller 48 and the battery 46. Thus, the grid 34, the sensor substrate 36 and the lead sheet 38 can easily be restored to a planar shape.

Additionally, since the shape-memory members 110a, 110b are arranged along the heat radiating line of the driving circuit ICs 112a, the reading circuit ICs 112b, the transceiver 50, the cassette controller 48 and the battery 46, upon operation of the driving circuit ICs 112a, the reading circuit ICs 112b, the transceiver 50, the cassette controller 48 and the battery 46, the grid 34, the sensor substrate 36 and the lead sheet 38 can reliably and effectively be restored to a planar shape.

Further, the screen 30 that contains the radiation detector 20 is capable of being wound up in a rolled shaped when radiation 14 is not applied thereto, and can be accommodated in a storage box or the like. On the other hand, when exposed to radiation 14, the screen 30 is unrolled and laid out in a flat shape by the shape-memory members 110a, 110b, so that handling of the radiation detecting cassette 10B can be improved dramatically.

Figure 18:
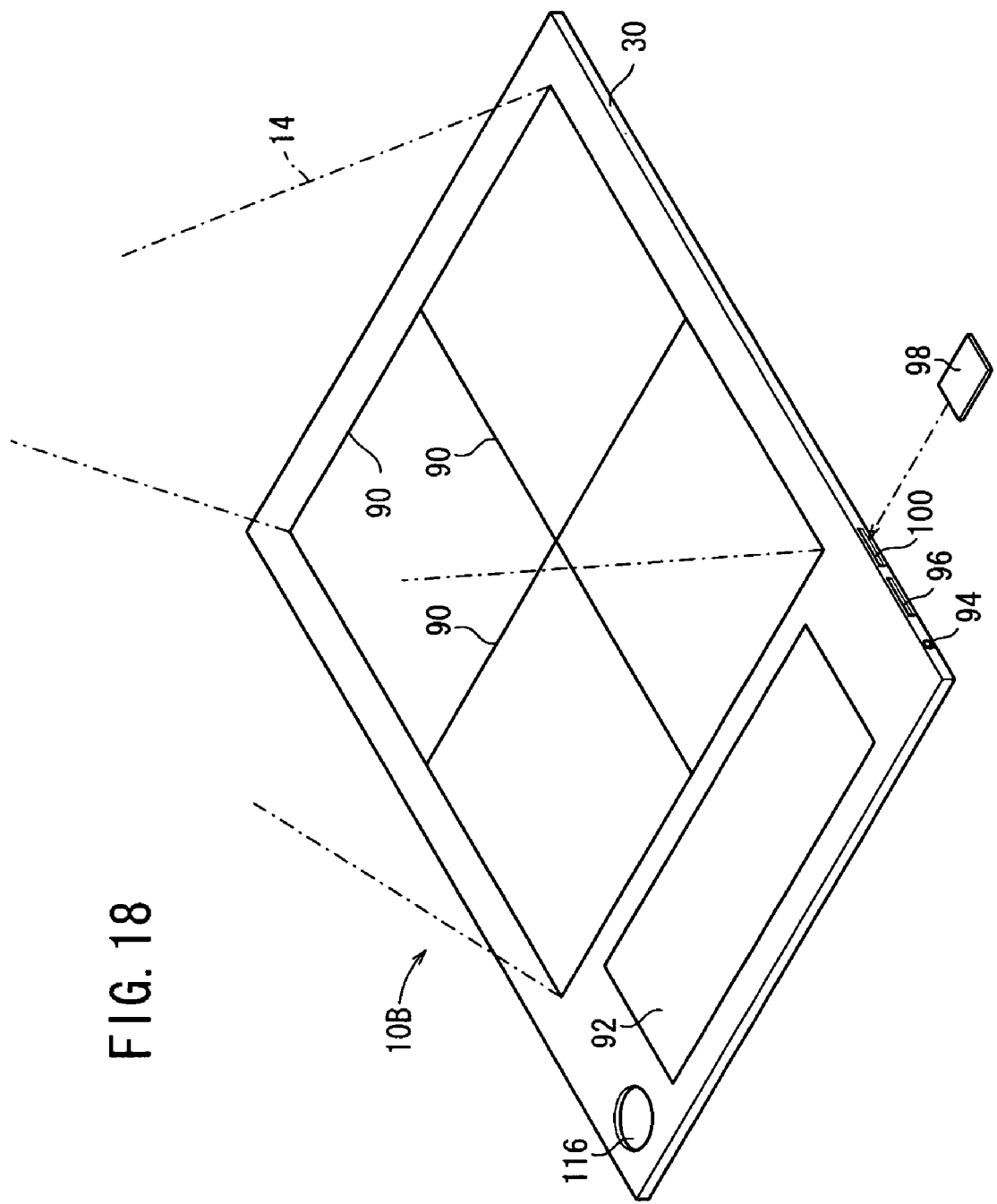
FIG. 18 is a perspective view showing another configuration of the radiation detecting apparatus according to the second embodiment.

Furthermore, similar to the radiation detecting cassette 10A of FIG. 10, when the radiation detecting cassette 10B is constructed as shown in FIG. 18, the same effects of the radiation detecting cassette 10A are obtained.

As shown in FIG. 18, a display unit 92 is disposed at a region outside of the image capturing area of the radiation detecting cassette 10B. Further, a hole 116 is formed in the screen 30, and by tying a cord or strap (not shown) through the hole 116, handling and portability of the radiation detecting cassette 10B can be facilitated.

Figure 19:
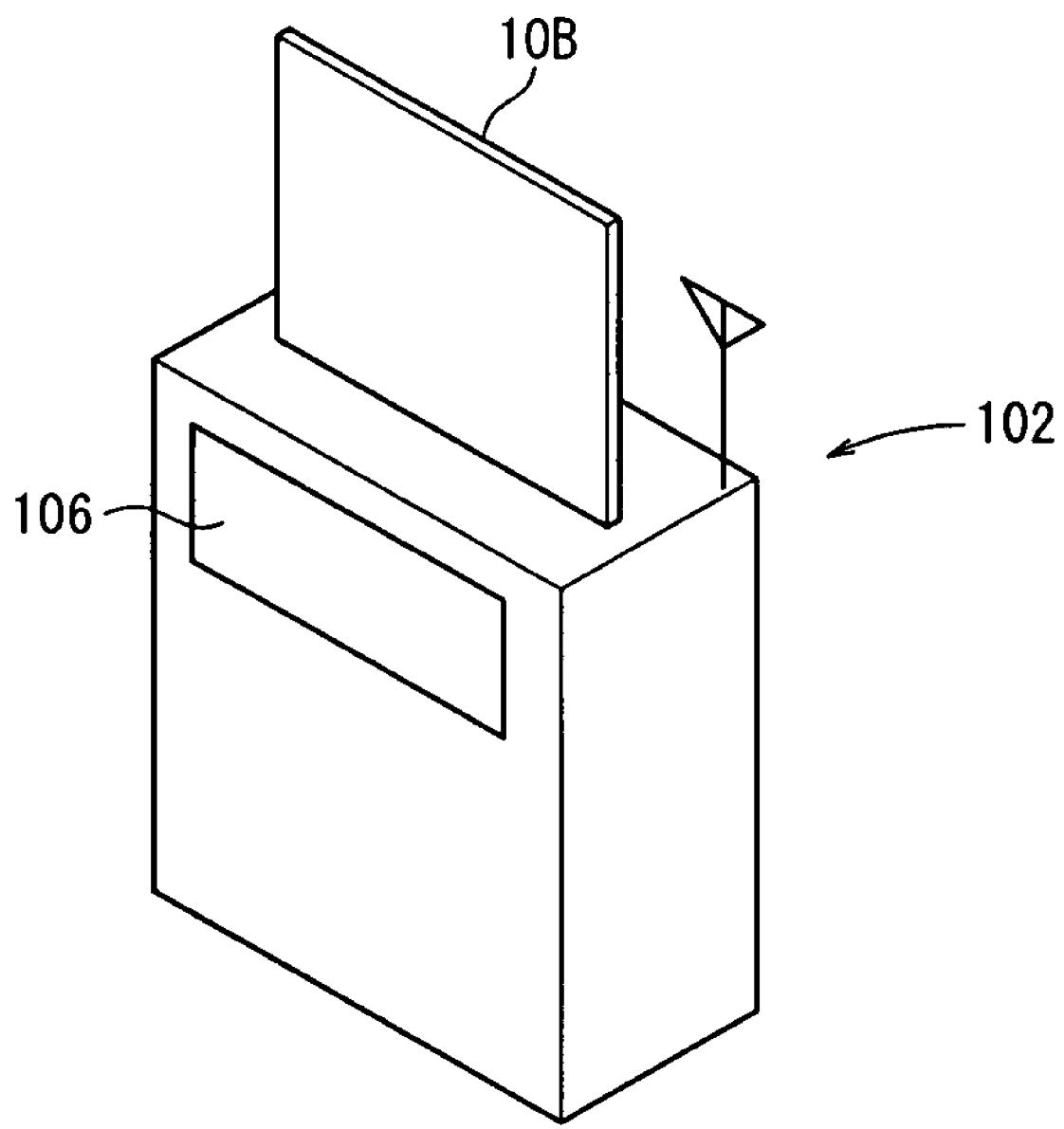
FIG. 19 is a perspective view of a cradle through which charging is performed with respect to the radiation detecting apparatus according to the second embodiment.
Figure 20A:
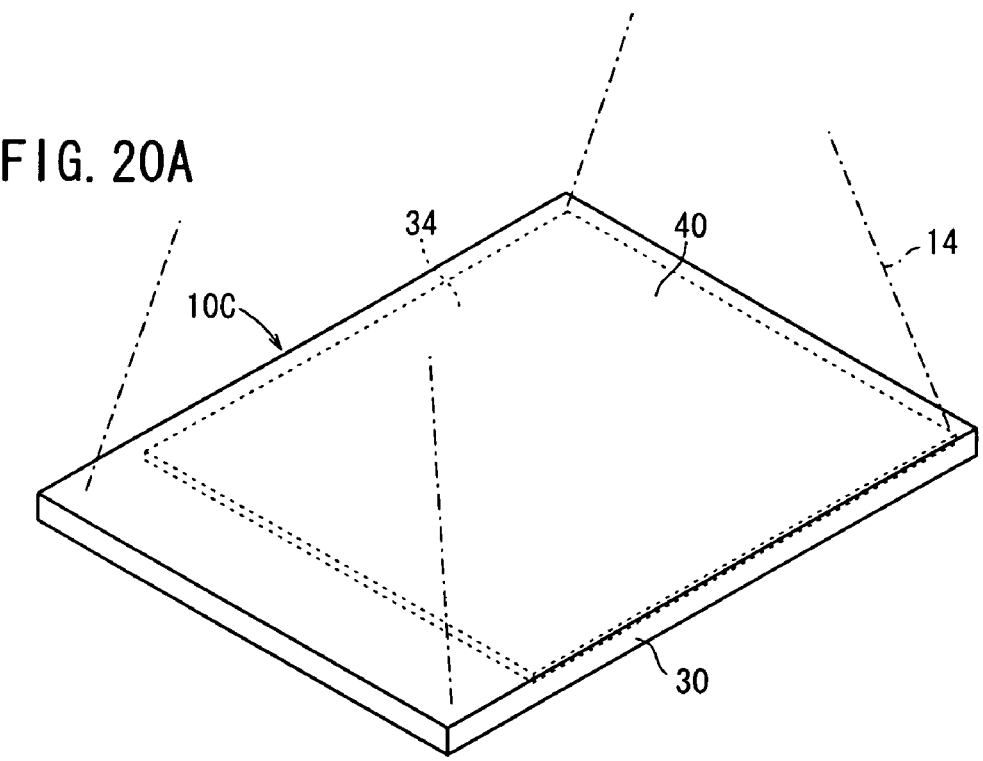
FIG. 20A and FIG. 20B are perspective views showing a radiation detecting apparatus according to a third embodiment of the present invention.
Figure 20B:
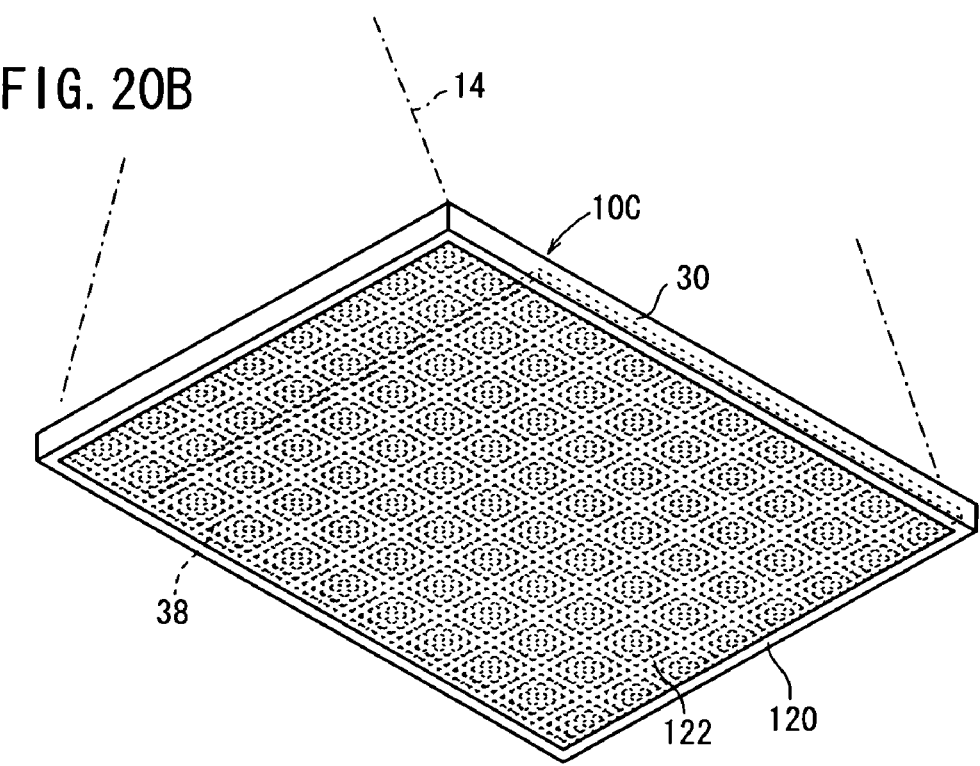
Figure 21:
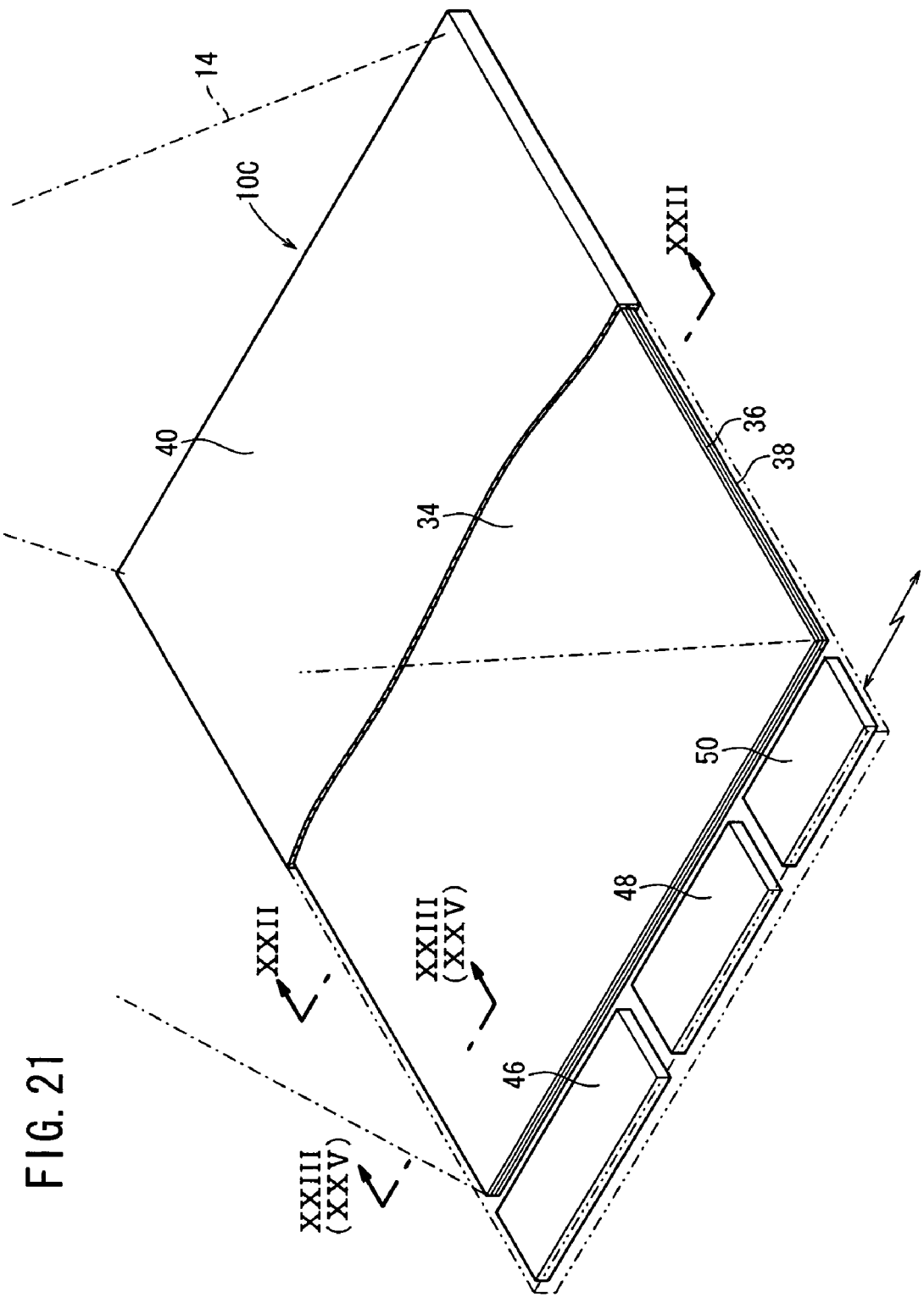
FIG. 21 is a perspective view, partially cut away, of the radiation detecting apparatus of FIGS. 20A and 20B.
Figure 22:
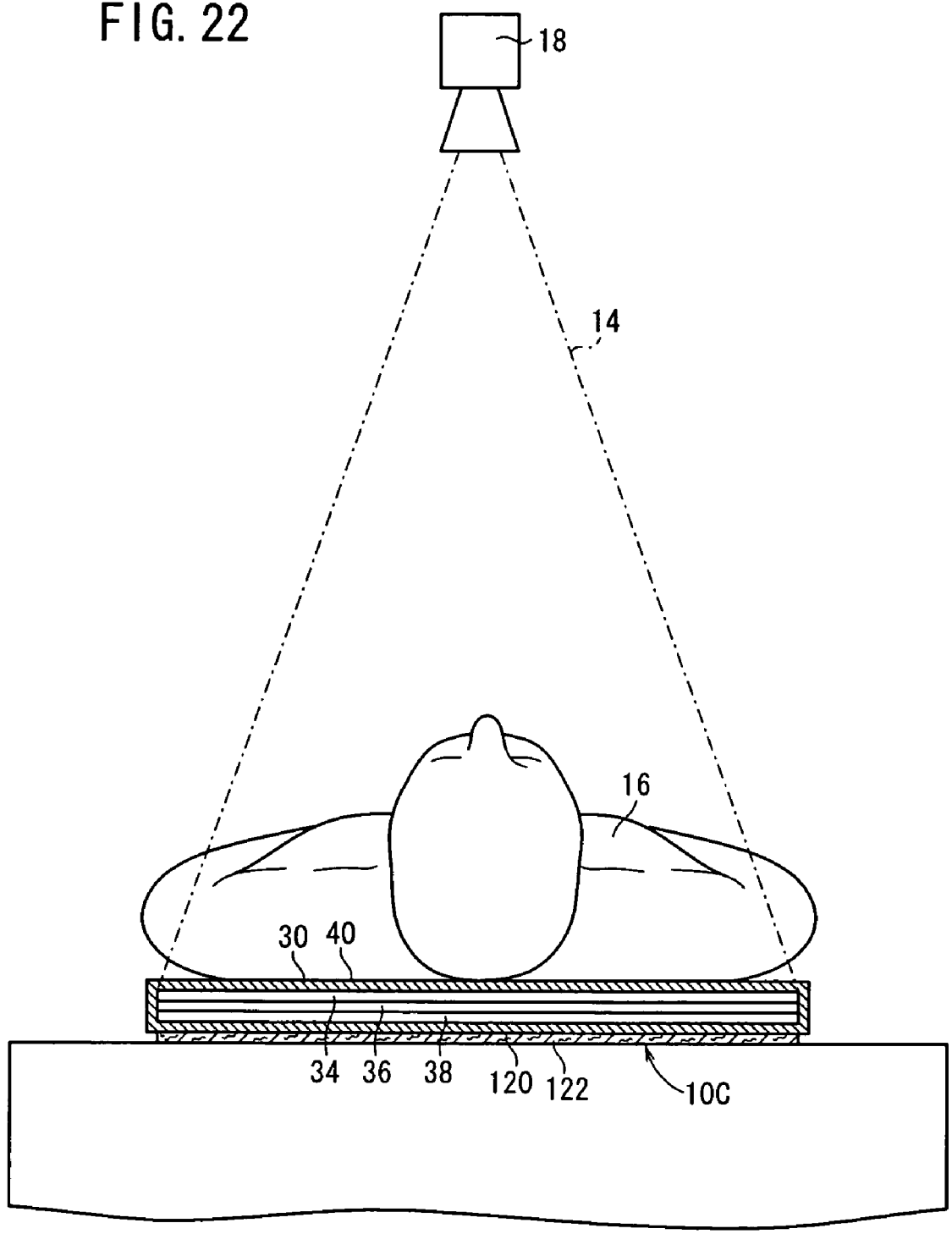
FIG. 22 is a cross-sectional view taken along line XXII-XXII of FIG. 21.
Figure 23:
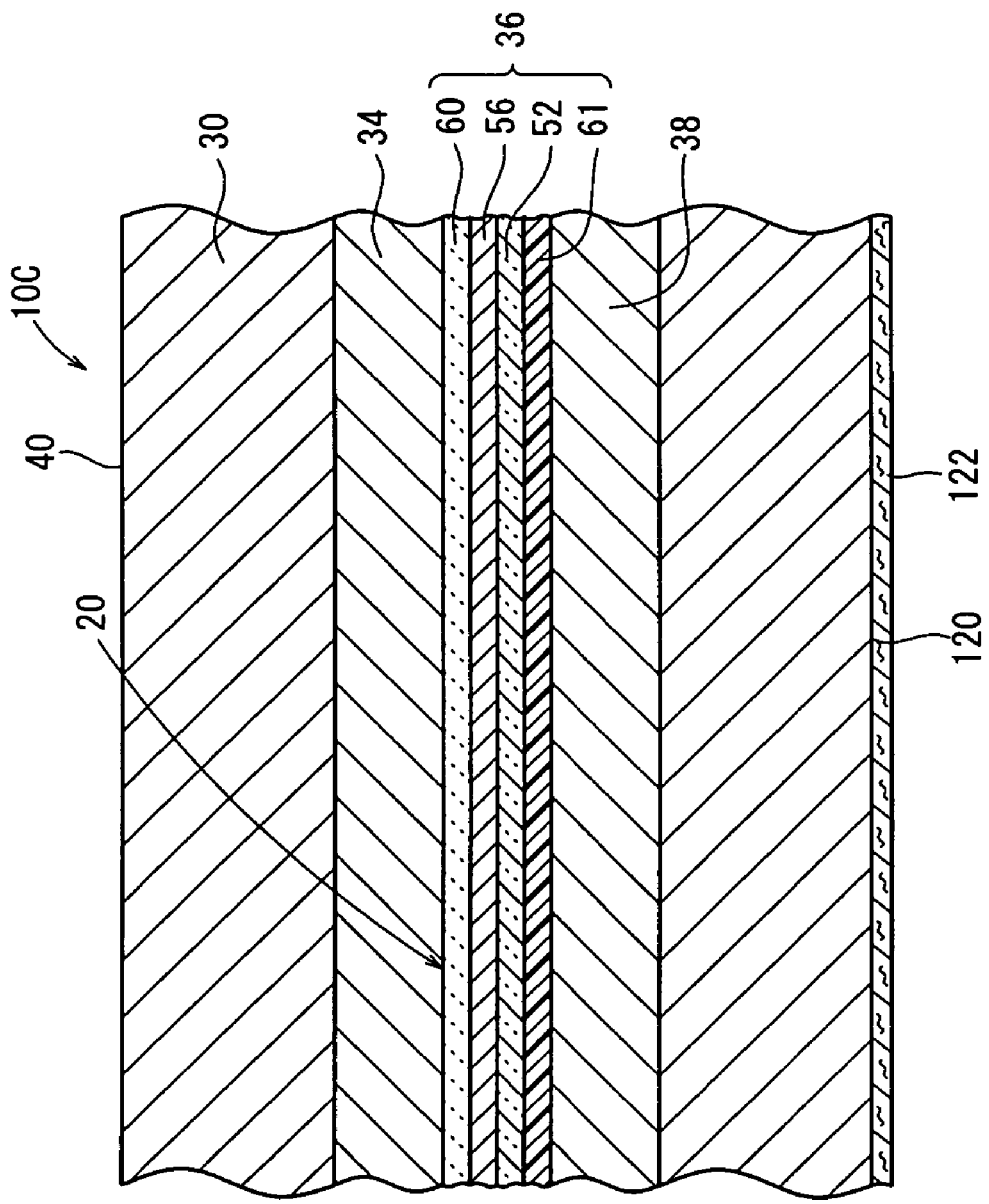
FIG. 23 is a cross-sectional view taken along line XXIII-XXIII of FIG. 21.

Similar to the case of FIG. 11, at a required location in an operating room or the hospital, a cradle 102 may be arranged, as shown in FIG. 19, which enables charging of the battery 46 in the radiation detecting cassette 10B to be carried out.

Next, a radiation detecting apparatus (radiation detecting cassette) 10C according to a third embodiment of the present invention, and a radiation image capturing system 12C incorporating the radiation detecting cassette 10C therein, will be described below with reference to FIGS. 20A through 25.

The radiation detecting cassette 10C and the radiation image capturing system 12C according to the third embodiment differ from the radiation detecting cassette 10A and the radiation image capturing system 12A according to the first embodiment (see FIGS. 1 to 11), and the radiation detecting cassette 10B and the radiation image capturing system 12B according to the second embodiment (see FIGS. 12 to 19), in that a protective sheet (protective member) 122 is attached to a surface 120 of the screen 30, which is opposite to the irradiated surface 40 thereof that faces toward the patient 16.

More specifically, if the radiation detecting cassette 10C and the radiation image capturing system 12C according to the third embodiment were represented as a block diagram, the basic features thereof are the same as those of the radiation detecting cassette 10A and the radiation image capturing system 12A according to the first embodiment, as well as those of the radiation detecting cassette 10B and the radiation image capturing system 12B according to the second embodiment. However, the third embodiment differs from the radiation detecting cassette 10A and the radiation image capturing system 12A of the first embodiment, and the radiation detecting cassette 10B and the radiation image capturing system 12B according to the second embodiment, in respect to the protective sheet 122 which is installed on the surface 120.

Basic differences between the radiation detecting cassette 10C and the radiation image capturing system 12C according to the third embodiment and the radiation detecting cassette 10A and the radiation image capturing system 12A according to the first embodiment, as well as differences from the radiation detecting cassette 10B and the radiation image capturing system 12B according to the second embodiment, have been described in outline form above. Next, specific structural features of the radiation detecting cassette 10C and the radiation image capturing system 12C according to the third embodiment shall be explained below in greater detail.

Figure 24:
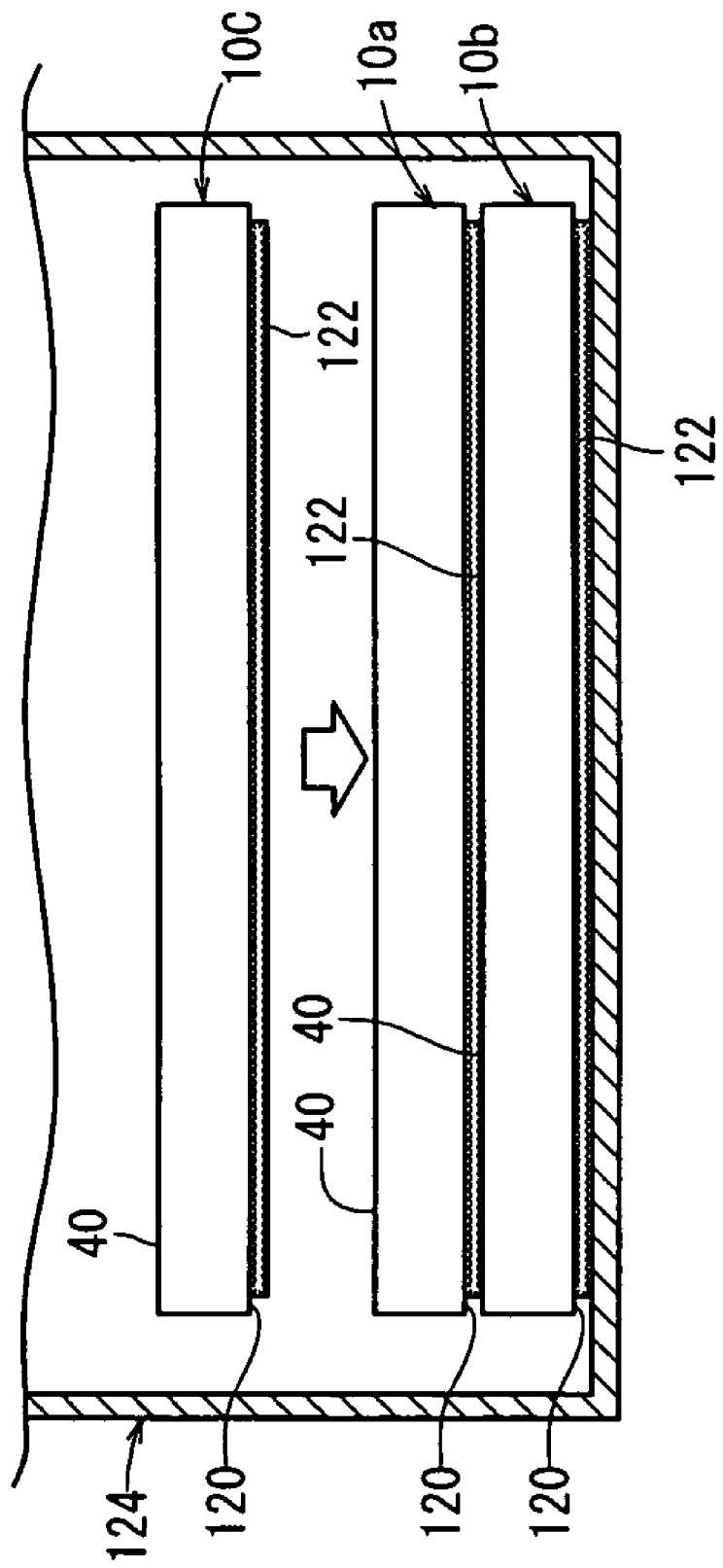
FIG. 24 is a front view, partially cut away, of a storage box, in which multiple radiation detecting apparatus are accommodated in an interior part thereof.
Figure 25:
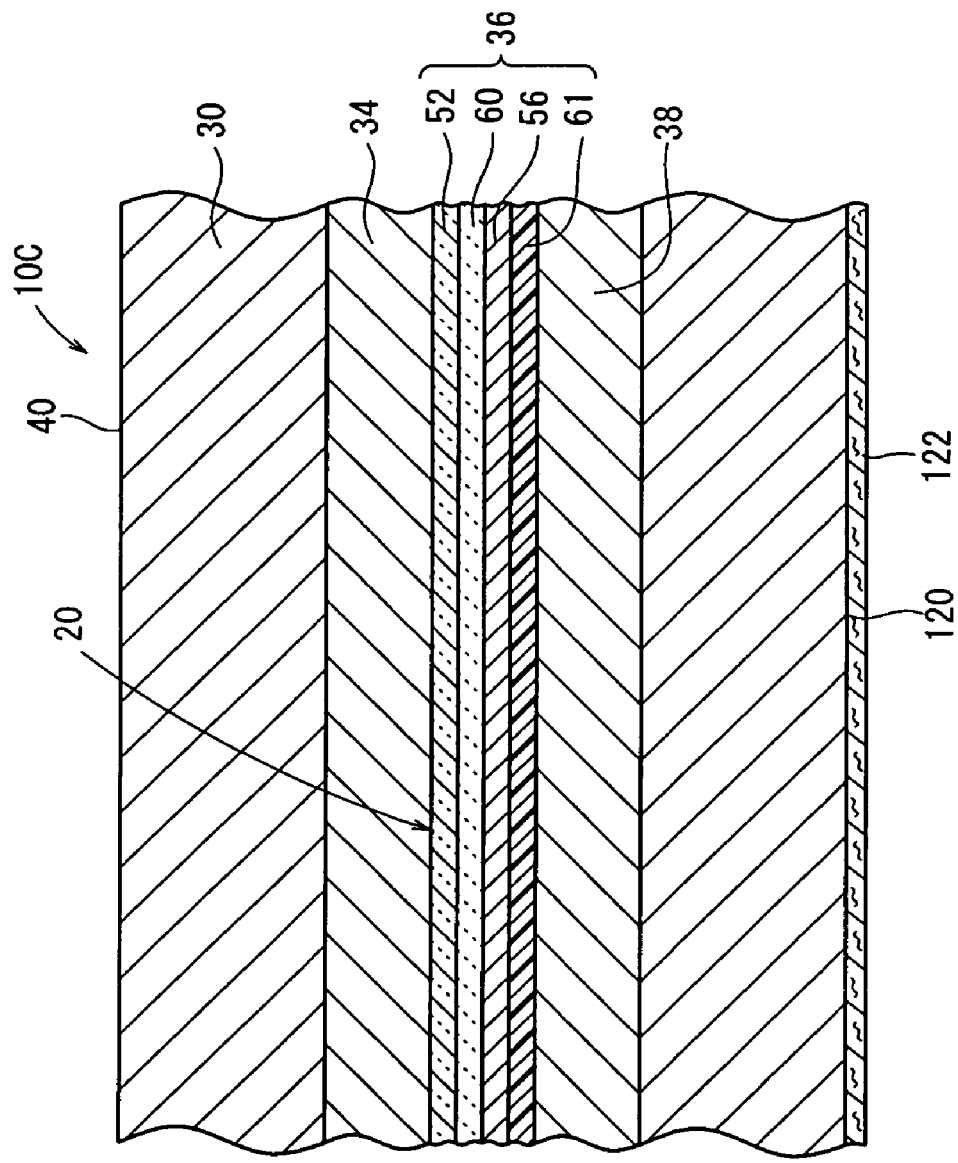
FIG. 25 is a cross-sectional view taken along line XXV-XXV of FIG. 21.

In the sheet-shaped radiation detecting cassette 10C shown in FIGS. 20A through 23, at a time when radiation 14 is not being applied to the patient 16 (when a radiation image is not being captured), a plurality of flexible screens 30, for example, are accommodated in a stacked condition inside a storage box 124 (see FIG. 24). On the other hand, when radiation 14 is applied with respect to the patient 16 (during image capturing), one of such screens 30 is laid out in a substantially flat planar shape with respect to the patient 16 (see FIGS. 21 and 22).

Further, on the screen 30, on a surface 120 thereof, which is opposite to the irradiated surface 40 on the side of the patient 16, a protective sheet 122 is attached. The protective sheet 122, for example, is made from a non-woven fabric having a predetermined thickness, which is formed as a flexible sheet and is adhered with respect to the surface 120 of the screen 30. More specifically, the protective sheet 122 is formed by non-woven entwined fibers, such as glass fibers, nylon fibers or the like.

Further, the protective sheet 122 is provided so as to cover entirely the surface 120 of the screen 30, wherein the coefficient of friction of the protective sheet 122 is less than the coefficient of friction of the screen 30.

The radiation detecting cassette 10C and the radiation image capturing system 12C according to the third embodiment are basically constructed as described above. Operations of the radiation detecting cassette 10C and the radiation image capturing system 12C will be described below.

For capturing radiation image information when the doctor performs a surgical operation in an operating room, when the doctor examines the patient, or when the doctor goes on rounds in the hospital, after patient information and the image capturing conditions have been registered, the doctor or a radiological technician, for example, takes an unused one of the radiation detecting cassettes 10C from the storage box 124. Then, the doctor or radiological technician positions the radiation detecting cassette 10C at a predetermined position between the patient 16 and a bed, for example, in a condition such that the irradiated surface 40 thereof faces toward the radiation source 18.

Next, after the radiation source 18 is moved suitably to a position confronting the radiation detecting cassette 10C, the doctor or radiological technician operates the image capturing switch of the radiation source 18, whereby image capturing with respect to the patient 16 is carried out in the same manner as in the first and second embodiments.

After completion of image capturing with respect to the patient 16, as shown in FIG. 24, the radiation detecting cassette 10C is accommodated inside the storage box 124 together with other radiation detecting cassettes 10a, 10b. At this time, the radiation detecting cassette 10C, for example, is accommodated in the storage box 124 by stacking on an upper portion of the other radiation detecting cassette 10a. However, since the non-woven protective sheet 122 is provided on the bottom surface of the newly-accommodated radiation detecting cassette 10C, the radiation detecting cassette 10C is stored in a stacked condition without causing damage to the irradiated surface 40 of the other radiation detecting cassette 10a, which becomes positioned underneath the radiation detecting cassette 10C.

In the event that the radiation detecting cassette 10C is accommodated in the storage box 124 before a radiation image of the patient 16 is captured, damage to the irradiated surface of another radiation detecting cassette, which is accommodated in the storage box 124 underneath the radiation detecting cassette 10C, can also be prevented.

As described above, with the radiation detecting cassette 10C and the radiation image capturing system 12C according to the third embodiment, the protective sheet 122 is provided on a surface 120 (lower surface) of the screen 30 constituting the radiation detecting cassette 10C, which is opposite to the irradiated surface 40 thereof irradiated with radiation 14. By forming the protective sheet 122 from a non-woven fabric, for example, even in the case that a plurality of radiation detecting cassettes 10C, 10a, 10b are stacked vertically and stored, damage to the irradiated surfaces 40 of the radiation detecting cassettes 10C, 10a caused by adjacent other radiation detecting cassettes 10a, 10b is reliably prevented. More specifically, when the radiation detecting cassettes 10C, 10a are stacked, the protective sheets 122 of the radiation detecting cassettes 10C, 10a are provided so as to be capable of protecting the irradiated surfaces 40 on other radiation detecting cassettes 10a, 10b positioned and stacked adjacent thereto.

As a result, a plurality of radiation detecting cassettes 10C, 10a, 10b can be stored in a stacked manner, and the radiation detecting cassettes 10C, 10a, 10b can be accommodated within a limited space.

Further, because the protective sheet 122 is disposed only on a surface 120 which is opposite to the irradiated surface 40 on the screen 30, when a radiation image is captured using the screen 30, application of radiation 14 thereto is not hindered, and any influence of the protective sheet 122 on the radiation image is avoided. As a result, a clear radiation image can be obtained without occurrence of scattering of the radiation 14, and while avoiding generation of noise and the like.

Furthermore, without providing the protective sheet 122 on the screen 30, the surface 120 of the screen 30 that is opposite from the irradiated surface 40 thereof may also be formed by a material having a coefficient of friction lower than that of the irradiated surface 40. The surface 120 may also be coated by a material having a low frictional resistance.

A radiation detecting apparatus 10D according to a fourth embodiment of the present invention and a radiation image capturing system 12D incorporating the radiation detecting apparatus 10D will be described below with reference to FIGS. 26 through 31.

The radiation detecting apparatus 10D and the radiation image capturing system 12D according to the fourth embodiment differs from the radiation detecting cassettes 10A to 10C and the radiation image capturing systems 12A to 12C of the first through third embodiments (see FIGS. 1 through 25) in that the radiation detecting apparatus 10D has a sealing protective film 130 made from a material permeable to radiation 14, which covers a portion or the entirety of at least the radiation detector 20.

More specifically, if the radiation detecting apparatus 10D and the radiation image capturing system 12D according to the fourth embodiment were represented as a block diagram, the basic features thereof are the same as those of the radiation detecting cassettes 10A to 10C and the radiation image capturing systems 12A to 12C according to the first through third embodiments. However, the fourth embodiment differs from the radiation detecting cassettes 10A to 10C and the radiation image capturing systems 12A to 12C of the first through third embodiments, in that a portion or the entirety of at least the radiation detector 20 is covered by the sealing protective film 130.

Basic differences between the radiation detecting apparatus 10D and the radiation image capturing system 12D according to the fourth embodiment and the radiation detecting cassettes 10A to 10C and the radiation image capturing systems 12A to 12C according to the first through third embodiments have been described in outline form above. Next, specific structural features of the radiation detecting apparatus 10D and the radiation image capturing system 12D according to the fourth embodiment shall be explained below in greater detail.

Figure 26:
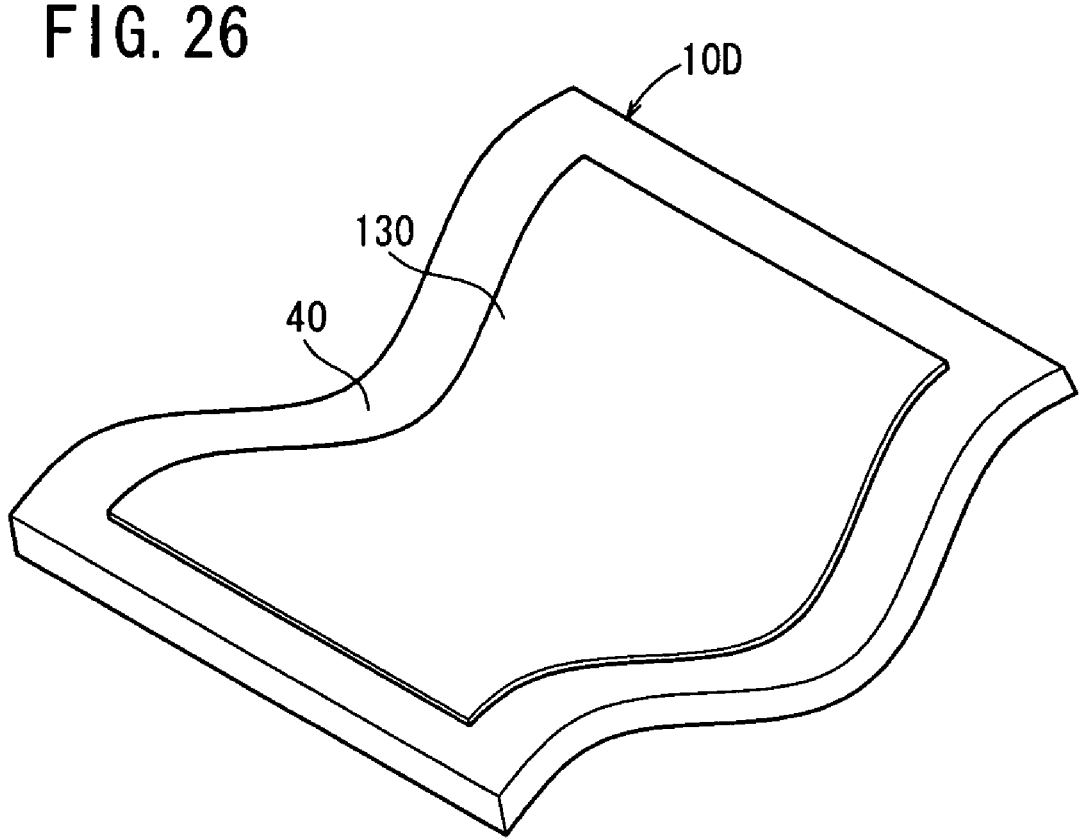
FIG. 26 is a perspective view of a radiation detecting apparatus according to a fourth embodiment of the present invention.
Figure 27:
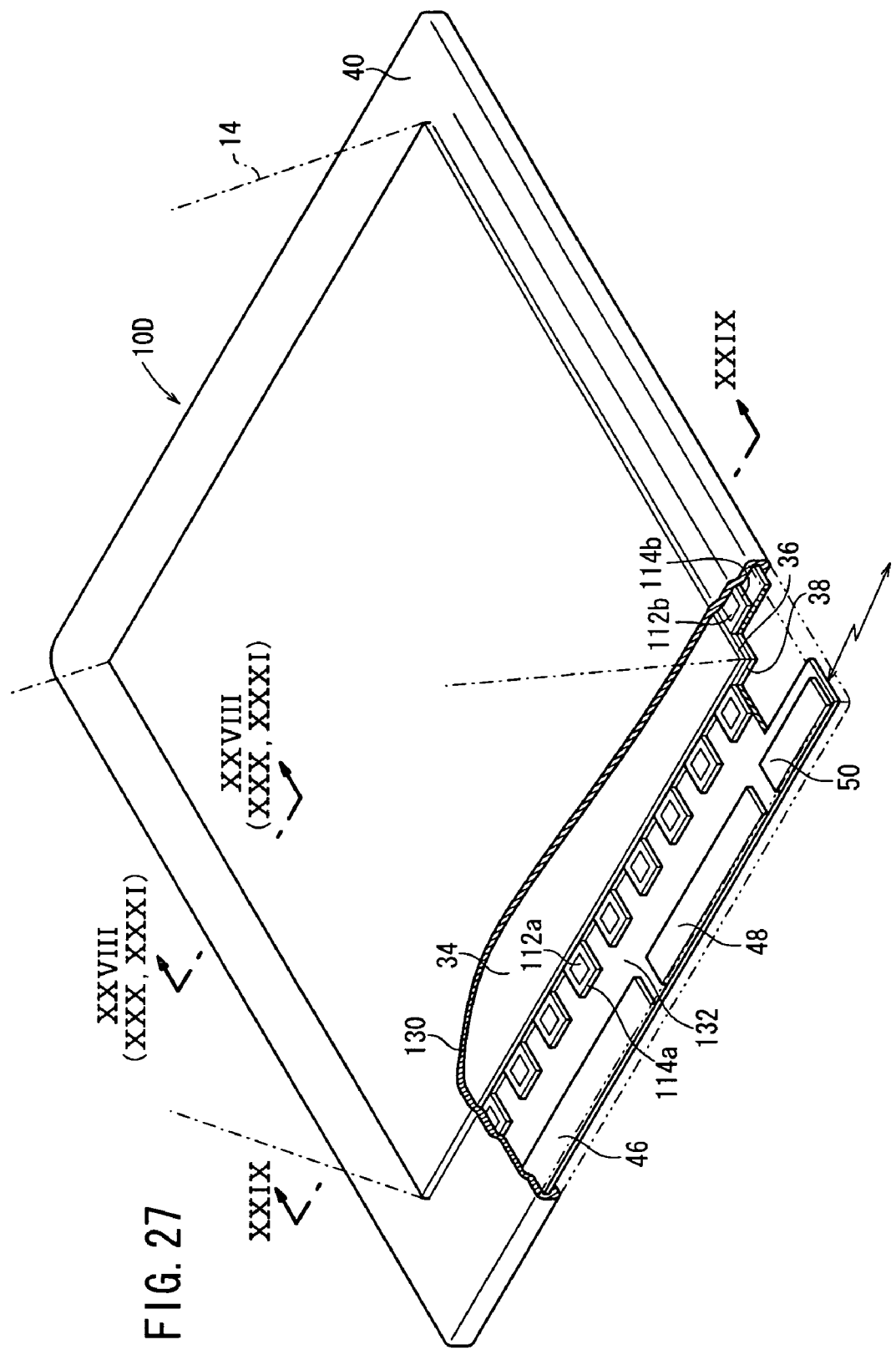
FIG. 27 is a perspective view, with partial omission, of the radiation detecting apparatus of FIG. 26.
Figure 28:
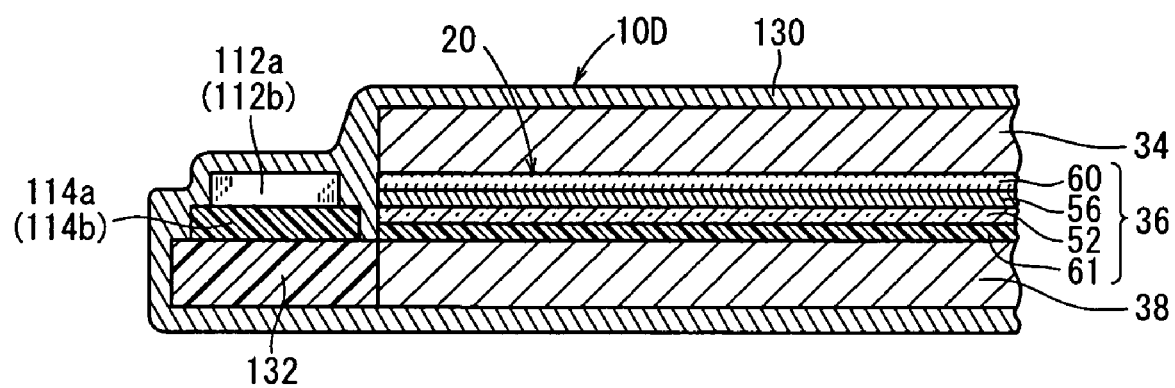
FIG. 28 is a cross-sectional view taken along line XXVIII-XXVIII of FIG. 27.

As shown in FIGS. 26 through 28, the radiation detecting apparatus 10D includes a sealing protective film 130 made from a material permeable to radiation 14, and which covers a portion or the entirety of at least the radiation detector 20. The radiation detecting apparatus 10D is flexible overall. Further, on the sealing protective film 130, at least a surface base material thereof is colored black and is opaque to light. In the example of FIGS. 27 and 28, the sealing protective film 130 is formed so as to cover the grid 34, the sensor substrate 36 and the lead sheet 38. Herein, the term "sealing" more specifically may include the meaning of covering a portion of the radiation detector 20 and the meaning of sealing the entirety of the radiation detector, i.e., "hermetically sealed", in order to improve waterproofing, moisture-proofing, and impact resistance of the flexible radiation detector 20.

Figure 29:
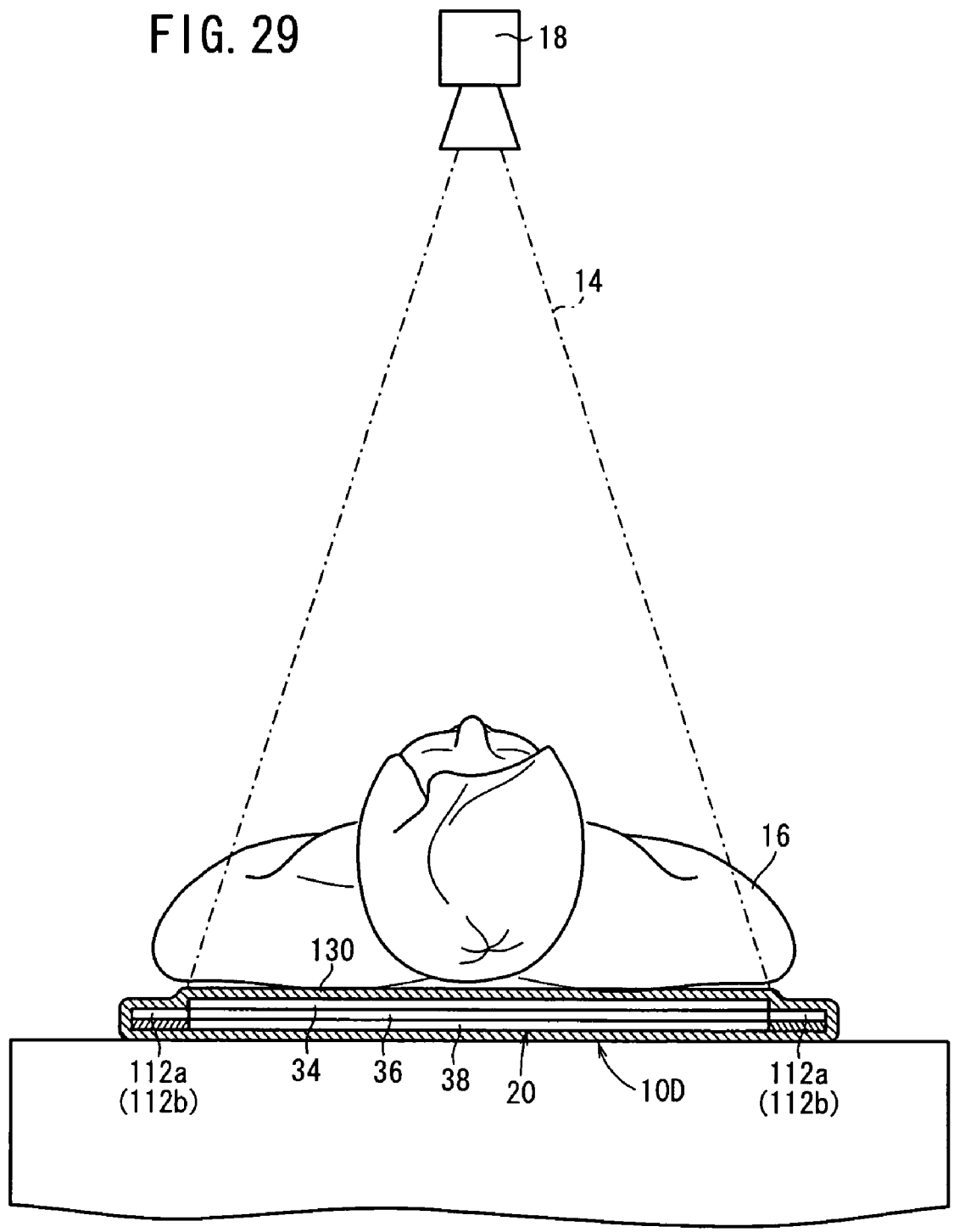
FIG. 29 is a cross-sectional view taken along line XXIX-XXIX of FIG. 27.

Accordingly, at a time when radiation 14 is not applied with respect to the patient 16 (when an image is not being captured), the radiation detecting apparatus 10D can be wound in a rolled-up shape and stored in a non-illustrated storage box or the like. On the other hand, as shown in FIG. 29, when radiation 14 is applied with respect to the patient 16 (during image capturing), the radiation detecting apparatus 10D is unrolled and laid out in a substantially flat form with respect to the patient 16.

Further, as shown in FIG. 27, a circuit substrate 132 is arranged along sides of the sensor substrate 36. On the circuit substrate 132, driving circuit ICs 112a mounted on circuit boards 114a, and reading circuit ICs 112b mounted on circuit boards 114b, are disposed respectively. Further, the battery 46, the cassette controller 48 and the transceiver 50 also are disposed on the circuit substrate 132.

On the other hand, concerning the sealing protective film 130, a method preferably is adopted by which a thin sheet material (film) is formed by laminating. In this case, the sealing protective film 130 may be formed by a hot laminating process or a cold laminating process. As hot laminating processes, there are known, for example, an extrusion laminating process, a dry laminating process, a non-solvent laminating process, and a heat-laminating process. As cold laminating processes, there are known, for example, an extrusion laminating process and a dry laminating process.

In the extrusion laminating process, various types of polymer films, paper, aluminum foil, or a laminate film thereof, are used as a base material, which are coated with an organic titanate, butadiene, or isocyanate anchor coating agent. Then, a molten polyolefin resin or the like is placed in an extrusion apparatus, an extruded film is formed by a T-die, and the film is pressure-bonded onto the base material.

In the dry laminating process, an adhesive including an isocyanate which has been diluted by a solvent is used, wherein such an adhesive is applied to various types of polymer films, paper, aluminum foil, or a laminate film thereof, and the solvent is removed upon drying. Then, while the adhesive still possesses an adhesive force, another polymer film, paper, aluminum foil, or laminate film thereof, is stacked thereon and such members are pressure bonded together.

In the non-solvent laminating process, a solventless adhesive including an isocyanate is heated to between 80° C. and 100° C., and is applied to various types of polymer films, paper, aluminum foil, or a laminate film thereof, in a state where viscosity thereof is low. Then, after applying, this and another polymer film, paper, aluminum foil, or laminate film thereof, are pressure-bonded together using a heat roll.

In the heat-laminating process, polymer films, or a metal plate of tin free steel or the like and a polymer film, which are desired to be bonded together, are pressure bonded by a heat roll, one or both of which are melted and heat bonded, thereby making both members integral.

In the case that a hot laminating process is used, preferably, a laminate film which can be formed by heating at a temperature of 180° C. or below, and more preferably 150° C. or below, is used.

The laminate film includes at least the surface base material, an intermediate base material, a coat layer and a sealant layer, which are stacked in this order. When the laminate film is applied at least on the radiation detector 20, the surface base material is positioned on the outer side, whereas the sealant layer is positioned on the inner side thereof.

As the surface base material, there may be used, for example, a polyester film of polyethylene terephthalate, polybutylene terephthalate or the like, a polyamide type film of nylon-6, nylon-6,6, polymethaxylyleneadipamide (N-MXD6) or the like, a polyolefin type film of low density polyethylene, high density polyethylene, linear low density polyethylene, polypropylene or the like, a polyacrylonitrile type film, a poly(meta)acryl type film, a polystyrene type film, a polycarbonate type film, an ethylene-vinyl alcohol copolymer (EVOH) type film, polyvinyl alcohol type film, a film implemented by coating a paper material, such as carton paper or the like, a metallic foil of aluminum or copper, etc., and various types of other materials using the same as a base material, with various polymers such as polyvinylidene chloride (PVDC) resin or polyvinyl alcohol resin, an ethylene-vinyl acetate copolymer resin, or an acryl type resin or the like, a film formed by evaporating a metal such as aluminum or the like, a film formed by dispersing a metallic fine powder, a film formed by dispersing an inorganic filler or the like, and a film to which an oxygen scavenging function is applied.

An inorganic filler can also be dispersed within the various polymers that are used as coatings.

As the inorganic filler, there may be used silica, alumina, mica, talc, aluminum flakes, glass flakes or the like, although a layered silicate of montmorillonite or the like is preferred. Further, as the dispersing method therefor, for example, a known method such as an extrusion/kneading method, or a mixing and dispersing method in a resin solution, may be used.

As the method for imparting an oxygen scavenging function, for example, a method may be given in which a composition containing a low molecular organic compound that reacts with oxygen, such as a hindered phenol, vitamin C, vitamin E, an organic phosphorus compound, gallic acid, pyrogallol or the like, or a transition metal compound such as cobalt, manganese, nickel, iron, copper or the like, is used at least in part.

The thickness of the aforementioned film materials should, in practice, be on the order of 10 µm to 300 µm, and more preferably on the order of 10 µm to 100 µm. In the case of a plastic film, a film stretched monoaxially or biaxially may be utilized.

The intermediate base material may be a silica vapor deposited layer or an alumina vapor deposited layer, which is formed by vapor deposition of silca or alumina on the aforementioned surface base layer. As the method for vapor deposition with respect to the surface base material, a physical vapor deposition process or chemical vapor deposition process may be used. Further, the silica vapor deposited layer or the alumina vapor deposited layer may be formed by binary deposition of silica and alumina.

As resins which are utilized for the coat layer, there may be used polyurethane type resins such as polyurethane resin, polyurethane-urea resin, acrylic modified urethane resin, acrylic modified urethane-urea resin or the like, vinyl chloride-vinyl acetate copolymerization based resin, rosin based resins such as rosin-modified maleic acid resin, polyamide based resin, polyester based resin, chlorinated olefin-based resins such as chlorinated polypropylene resin, polyethylene imine based resin, polybutadiene resin, and an organic titanium based resin. Such resins may be dissolved in water, methanol, ethanol, 2-propanol, ethyl acetate, methyl ethyl ketone, toluene or the like, and can be formed as the coat layer by applying the same using a gravure process, a roll coat process, or the like. When forming the coat layer, general-use printing equipment, such as conventional gravure printing apparatus, flexo-printing apparatus, offset printing apparatus, etc., which have been used for printing of polymer films, may be applied and utilized in a similar manner.

In practice, the thickness of the coat layer preferably is 0.005 µm to 5 µm, and more preferably 0.01 µm to 3 µm. If the thickness is less than 0.005 µm, adhesion becomes difficult to achieve, whereas if the thickness is greater than 5 µm, it is difficult to form the resin layer with uniform thickness.

In the event that a curable material is used for the coat layer, a one-pack type or a two-pack type curable resin may be used, although in the case that water resistance and resistance to heat are desired, use of a two-pack type curable resin is more practical.

For imparting other additional functions to the coat layer, additive agents may be included in the above-mentioned resins. For example, to improve friction resistance (rub resistance), antiblocking, slip characteristics, improve heat resistance, or to prevent static charge, various waxes, dispersing agents, antistatic agents, or surface modifying agents may be included and can be suitably selected and used.

As the sealant layer, use of a flexible polymer film is preferred. In view of the development of favorable heat-sealing characteristics, a polyethylene film or a polypropylene film, or a polyolefin based film made up of an ethylene/vinyl acetate copolymer or the like, is preferably selected. In practice, the thickness of such films preferably is 10 µm to 300 µm, and more preferably 10 µm to 100 µm. Various surface processes may be implemented on the film surface, such as a corona discharge treatment or a flame treatment.

The radiation detecting apparatus 10D and the radiation image capturing system 12D according to the fourth embodiment are basically constructed as described above. Operations of the radiation detecting apparatus 10D and the radiation image capturing system 12D will be described below.

For capturing radiation image information when the doctor performs a surgical operation in an operating room, when the doctor examines the patient, or when the doctor goes on rounds in the hospital, after patient information and image capturing conditions have been registered, the doctor or a radiological technician removes a rolled radiation detecting apparatus 10D from a storage box (not shown) and positions the radiation detecting apparatus 10D at a predetermined position between the patient 16 and a bed, for example, in a condition such that the irradiated surface 40 thereof faces toward the radiation source 18. At this time, due to the fact that the sealing protective film 130 is opaque to light, incidence of external light (fluorescent light, etc.) on the radiation detector 20 is blocked, and generation of extraneous electrical charges due to such external light can be reduced.

Next, when the doctor or radiological technician turns on the power switch of the radiation detecting apparatus 10D, supply of power to the radiation detector 20, the cassette controller 48 and the transceiver 50 from the battery 46 is started, and operations of the driving circuit ICs 112a, the reading circuit ICs 112b, the cassette controller 48 and the transceiver 50 are initiated.

Then, after the radiation source 18 has been suitably moved to a position confronting the radiation detecting apparatus 10D, and the doctor or radiological technician operates the image capturing switch of the radiation source 18, image capturing is performed with respect to the patient 16 in the same manner as in the first through third embodiments.

After a radiation image of the patient 16 has been captured, when the doctor or radiological technician turns off the power switch, supply of electrical power from the battery 46 to the radiation detector 20, the cassette controller 48 and the transceiver 50 is halted, and operations of the driving circuit ICs 112a, the reading circuit ICs 112b, the cassette controller 48 and the transceiver 50 are brought to an end. Thereafter, the doctor or radiological technician winds the radiation detecting apparatus 10D in a rolled shape, whereby the radiation detecting apparatus 10D can be accommodated in a storage box.

As described above, in accordance with the radiation detecting apparatus 10D and radiation image capturing system 12D of the fourth embodiment, because the sealing protective film 130 is formed so as to cover the grid 34, the sensor substrate 36 and the lead sheet 38, waterproofing, moistureproofing, and impact resistance of the flexible radiation detector 20 can be improved, and reliability of the radiation detecting apparatus 10D can be enhanced. Accordingly, when the radiation detecting apparatus 10D is used in an operating room or the like, although blood stains and other contaminants may be attached to the radiation detecting apparatus 10D, because the radiation detecting apparatus 10D is configured to be water and moisture resistant as well as impact resistant and also to have a sealed structure, the radiation detecting apparatus 10D can be subjected to antiseptic cleaning as necessary, so that it can be used repeatedly and continuously, which also leads to lowering running costs thereof.

Further, with the fourth embodiment, in the event that the sealing protective film 130 is formed by a hot laminating process, because a sealing protecting film 130 is used which can be formed at an applied heating temperature of 180° C. or lower, and more preferably 150° C. or lower, when laminated, any adverse influence of heat on the scintillator 52 or on the various circuit elements constituting the radiation detector 20 can be avoided. Further, since the sealing protective film 130 is opaque to light, the influence of external light on the radiation detector 20 can be reduced.

By using a film coated with a metallic foil of aluminum, copper or the like, a film on which a metal such as aluminum or the like is vapor deposited, or a film on which a metallic powder is dispersed, for example, as the surface base material for the sealing protective film 130, since the sealing protective film 130 is made conductive, the influence of external electric waves or static electricity on the radiation detector 20 can be reduced, thus enabling a high signal-to-noise ratio (S/N) for the radiation image information. In this case, an antenna of the transceiver 50 preferably projects outside of the sealing protective film 130.

Furthermore, since the radiation detecting apparatus 10D incorporating the radiation detector 20 therein is capable of being wound in a rolled shaped when radiation 14 is not being applied thereto, and can be accommodated in a storage box or the like, ease of handling the radiation detecting apparatus 10D can be improved dramatically.

Figure 30:
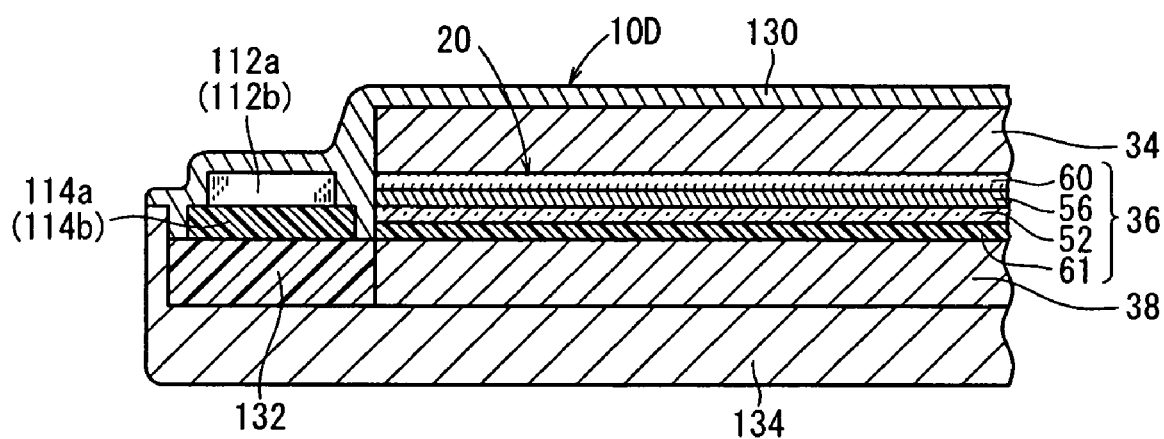
FIG. 30 is a cross-sectional view taken along line XXX-XXX of FIG. 27.

In the example described above, an example has been shown in which the sealing protective film 130 is formed to cover the grid 34, the sensor substrate 36 and the lead sheet 38. However, apart therefrom, as shown in FIG. 30, the lead sheet 38, the sensor substrate 36 and the grid 34 may be accommodated inside a box-shaped casing 134 with an upper surface opening, and further wherein the sealing protective film 130 is formed so as to cover the grid 34 and the sensor substrate 36. In this case, a heat pressure bonding process can be used under a reduced pressure. For example, a stacked body, which is made up of the grid 34, the sensor substrate 36 and the lead sheet 38 accommodated together within the casing 134, initially is accommodated inside an up/down split type chamber. After the chamber has been hermetically sealed and subjected to a vacuum to carry out defoaming of the stacked body, a laminate film is pressed onto an upper portion of the stacked body by a diaphragm. Further, by heat bonding the stacked body and the laminate film together, the sealing protective film 130 can be formed so as to cover the grid 34 and the sensor substrate 36.

Figure 31:
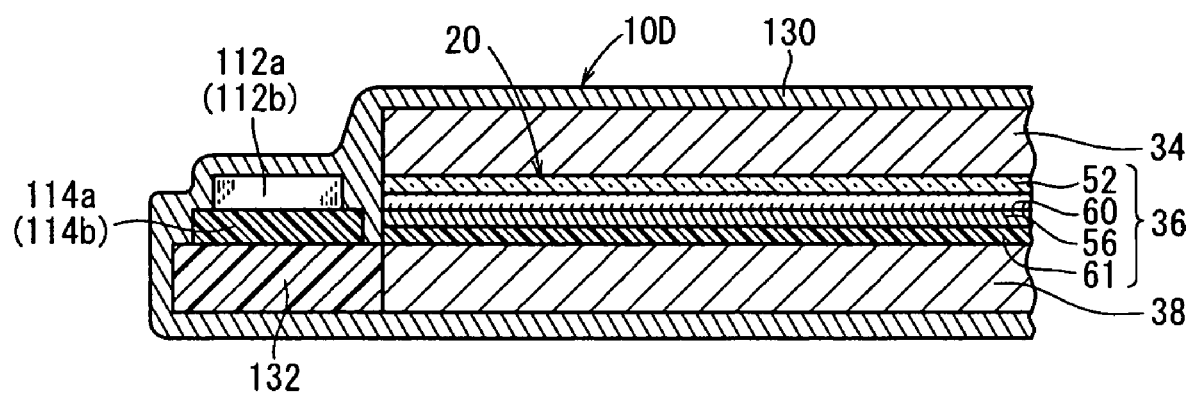
FIG. 31 is a cross-sectional view taken along line XXXI-XXXI of FIG. 27.

Further, according to the fourth embodiment, the stacked structure of the radiation detector 20 may be replaced by the structure shown in FIG. 31. As shown in FIG. 31, a TFT layer 56, a photoelectric transducer layer 60, and a scintillator 52 are stacked successively in this order from the substrate 61 toward the irradiated surface 40. In this case as well, since visible light converted by the scintillator 52 can be converted into electric signals by the photoelectric transducer layer 60, the same effects and advantages as those described above can be attained.

The present invention is not limited to the aforementioned embodiments, and it should be understood that various changes and modifications may be made to the embodiments without departing from the scope of the invention as set forth in the appended claims.

What is claimed is:

1. A radiation detecting apparatus comprising:
   a flexible radiation conversion panel for detecting radiation that has passed through a subject and converting the detected radiation into radiation image information; and
   a grip disposed on an end of the radiation conversion panel, a hardness of the grip being greater than that of the radiation conversion panel,
   wherein a hole is provided in the grip for enabling the grip to be gripped, and wherein the grip has therein a wireless communication unit for performing wireless communication with an external circuit, a controller for controlling the radiation conversion panel, and a battery for energizing the radiation conversion panel, the controller, and the wireless communication unit.

2. A radiation detecting apparatus according to claim 1, wherein the radiation conversion panel is housed in a flexible screen.

3. A radiation detecting apparatus according to claim 2, wherein the radiation detecting apparatus comprises a radiation detecting cassette, and the screen is made of a material permeable to the radiation.

4. A radiation detecting apparatus according to claim 2, wherein an irradiated surface of the screen includes a marker serving as a reference mark for an image capturing area and an image capturing position with respect to the subject.

5. A radiation detecting apparatus according to claim 1, wherein the radiation conversion panel includes a sensor substrate for converting the radiation into electrical signals, the sensor substrate comprising a scintillator for converting the radiation into visible light, and a plurality of solid-state detectors for converting the visible light into the electric signals.

6. A radiation detecting apparatus according to claim 5, wherein the solid-state detectors and the scintillator are successively arranged in order toward the subject, or the scintillator and the solid-state detectors are successively arranged in order toward the subject.

7. A radiation detecting apparatus according to claim 1, wherein two of the grips are disposed respectively on opposite ends of the radiation conversion panel, the radiation detecting apparatus being accommodated inside a storage box by hanging one of the grips on a hook, in a condition where the one grip is disposed upwardly and the other grip is disposed downwardly.

8. A radiation detecting apparatus according to claim 1, wherein a display unit for displaying information concerning the radiation detecting apparatus is disposed on the grip.

9. A radiation detecting apparatus according to claim 1, wherein at least one of an input terminal of an AC adapter for externally supplying power to the radiation detecting apparatus, a USB (Universal Serial Bus) terminal for sending and receiving information to and from an external circuit by way of wired communications, and a card slot for receiving a memory card and recording information therein is disposed in the grip.

10. A radiation detecting apparatus according to claim 1, wherein the radiation detecting apparatus is inserted into a cradle, in a condition where the irradiated surface irradiated by the radiation on the radiation conversion panel is substantially vertical, for carrying out charging with respect to the radiation detecting apparatus.

11. A radiation image capturing system comprising:
a radiation source for emitting radiation;
a radiation detecting apparatus comprising a flexible radiation conversion panel for detecting the radiation that has passed through a subject and converting the detected radiation into radiation image information, and a grip on an end of the radiation conversion panel, a hardness of the grip being greater than that of the radiation conversion panel, wherein a hole is provided in the grip for enabling the grip to be gripped; and
a first controller for controlling the radiation source and the radiation detecting apparatus,
wherein the grip has therein: (a) a wireless communication unit for performing wireless communication with an external circuit, (b) a second controller for controlling the radiation conversion panel, and (c) a battery for energizing the radiation conversion panel, the second controller and the wireless communication unit.

12. A radiation image capturing system according to claim 11, wherein the radiation detecting apparatus sends the radiation image information converted by the radiation conversion panel to the first controller by way of wireless communications.

* * * * *